US010925846B2

(12) United States Patent
Gagnon et al.

(10) Patent No.: US 10,925,846 B2
(45) Date of Patent: Feb. 23, 2021

(54) PHENYLKETONE CARBOXYLATE COMPOUNDS AND PHARMACEUTICAL COMPOSITIONS FOR THE PREVENTION AND TREATMENT OF OSTEOPOROSIS

(71) Applicant: Liminal BioSciences Limited, Cambridge (GB)

(72) Inventors: Lyne Gagnon, Laval (CA); Brigitte Grouix, Montreal (CA)

(73) Assignee: LIMINAL BIOSCIENCES LIMITED, Cambridge (GB)

( * ) Notice: Subject to any disclaimer, the term of this patent is extended or adjusted under 35 U.S.C. 154(b) by 383 days.

(21) Appl. No.: 15/516,635

(22) PCT Filed: Oct. 8, 2015

(86) PCT No.: PCT/CA2015/000530
§ 371 (c)(1),
(2) Date: Apr. 3, 2017

(87) PCT Pub. No.: WO2016/054725
PCT Pub. Date: Apr. 14, 2016

(65) Prior Publication Data
US 2019/0038580 A1  Feb. 7, 2019

Related U.S. Application Data

(60) Provisional application No. 62/062,660, filed on Oct. 10, 2014.

(51) Int. Cl.
| | | |
|---|---|---|
| *A61K 31/192* | (2006.01) | |
| *A61K 31/20* | (2006.01) | |
| *A61K 31/13* | (2006.01) | |
| *A61K 31/275* | (2006.01) | |
| *A61K 31/662* | (2006.01) | |
| *A61K 38/16* | (2006.01) | |
| *A61P 19/08* | (2006.01) | |
| *A61P 19/10* | (2006.01) | |

(52) U.S. Cl.
CPC ............ *A61K 31/192* (2013.01); *A61K 31/20* (2013.01); *A61P 19/08* (2018.01); *A61P 19/10* (2018.01); *A61K 31/13* (2013.01); *A61K 31/275* (2013.01); *A61K 31/662* (2013.01); *A61K 38/16* (2013.01); *A61K 2300/00* (2013.01)

(58) Field of Classification Search
CPC ...... A61K 31/192; A61K 31/20; A61K 31/13; A61K 31/275; A61K 31/662; A61K 38/16; A61P 19/08; A61P 19/10
See application file for complete search history.

(56) References Cited

U.S. PATENT DOCUMENTS

2012/0270787 A1* 10/2012 Doschak ................ A61K 38/23
514/11.9

FOREIGN PATENT DOCUMENTS

| WO | 2012/055014 A1 | 5/2012 |
| WO | 2012/097427 A1 | 7/2012 |
| WO | 2012/097428 A1 | 7/2012 |

OTHER PUBLICATIONS

Iannitti et. al., American Journal of Therapeutics, 2012, Lippincott Williams & Wilkins, vol. 19, pp. 228-246 (Year: 2012).*
International Search Report and Written Opinion for corresponding Application No. PCT/CA2015/000530 (dated Feb. 8, 2016).
Roncucci et al., "The In vitro Action of Bufexamac and Selected Hydroxamic Acids on Isolated Rat Liver Lysosomes," Archives Internationales de Pharmacodynamie et de Therpaie 203:348-367 (1973).

* cited by examiner

*Primary Examiner* — Sarah Pihonak
(74) *Attorney, Agent, or Firm* — Troutman Pepper Hamilton Sanders LLP (Rochester)

(57) ABSTRACT

The present invention concerns the use of compounds for preventing and/or treating osteoporosis, for stimulating bone formation, for stimulating the differentiation and mineralization of osteoblasts, or for inhibiting bone resorption in a subject. These novel uses have been found for compounds represented by Formula I and pharmaceutically acceptable salts thereof. wherein: $R_1$ and $R_2$ are independently equal to H, F or OH; A is $(CH_2)_m COOH$, $W(CH2)mCOOH$, or Y—CH(COOH)—(CH2)p-CH3 when B is H; or B is (CH2)mCOOH, W(CH2)mCOOH, or Y—CH(COOH)—$(CH_2)_p$—$CH_3$ when A is H; or A and B are covalently bonded to form a five (5), six (6), or seven (7)-membered cycloalkyl substituted with COOH; where: Y is O, S, HN or $CH_2$; W is 0, S or NH; m is 0-2; and p is 3-7; D is $CO(CH_2)_n CH_3$ or $CHOH(CH_2)nCH_3$ or $O(CH_2)_n CH_3$ where n is 2-6; and E is H or F.

17 Claims, 5 Drawing Sheets

PHENYLKETONE CARBOXYLATE COMPOUNDS AND PHARMACEUTICAL COMPOSITIONS FOR THE PREVENTION AND TREATMENT OF OSTEOPOROSIS

This application is a national stage application under 35 U.S.C. § 371 of PCT Application No. PCT/CA2015/000530, filed Oct. 8, 2015, which claims the priority benefit of U.S. Provisional Patent Application Ser. No. 62/062,660, filed Oct. 10, 2014.

FIELD OF INVENTION

The present invention relates to the field of medicine. Particular aspects of the invention relates to compounds, pharmaceutical compositions and uses thereof for the prevention or treatment of osteoporosis.

BACKGROUND OF INVENTION

Bone is a highly dynamic tissue which is constantly turned over and replaced by a process which is known as bone remodeling. The ability to remodel bone ensures that old bone or damaged tissue is renewed and that the architecture of the skeleton can most efficiently adapt to mechanical demands. Bone remodeling commences with the removal of old bone by osteoclast cells in a resorption phase lasting several weeks. Osteoblasts then migrate to the erosion cavity and deposit new bone over three or four months. In the normal skeleton, bone remodeling couples the activities of the osteoclast and osteoblast cells such that the amount of new bone laid down is equal to the bone that was removed, thereby maintaining a healthy bone mass. However, if bone resorption exceeds bone formation, there is a net loss of bone. The resultant condition, osteoporosis, is characterized by excessive bone resorption and subsequent low bone mass with increased bone fragility.

Osteoporosis is the general term used for diseases of the bone of diverse etiology that are characterized by a reduction in the mass of bone per unit volume to a level below that required for adequate mechanical support (Krane, S. M. et al., "Metabolic Bone Disease" in Harrison's Principles of Internal Medicine, page 1889, Edition 11 (1987)). One form of osteoporosis is senile osteoporosis which is responsible for a large portion of the health dollars spent on the geriatric population (Resnick, N. M. et al. "Senile Osteoporosis Reconsidered", JAMA 261, 1025-1029 (1989)). The two other most common forms of osteoporosis are peri- or postmenopausal osteoporosis and corticosteroid induced osteoporosis. Patients with chronic kidney disease (CKD) may develop bone diseases which can include osteoporosis as a result of changes in mineral metabolism and subsequent alterations in bone structure. Most often these changes worsen with progressive loss of kidney function. Indeed, and as summarized in the paragraph below, a number of pathological conditions can occur which increase the probability of the development of osteoporosis. Osteomalacia-like osteoporosis shares many of the symptoms of osteoporosis such as loss of calcium. Osteopenia refers to a lower than normal bone density but not as low as that observed in osteoporosis. It is considered to be a precursor to osteoporosis. Osteogenesis imperfecta is a congenital bone disorder characterized by brittle bones prone to bone fracture. Osteopetrosis is a rare inherited disease whereby the bones harden but are more brittle than normal. Osteonecrosis is a disease that causes bone death and collapse due to loss of blood supply to the bone. Paget's disease of bone is caused by excessive degradation and formation of bone followed by disorganized bone remodeling.

As is known, various diseases and conditions may cause osteoporosis: autoimmune diseases which include rheumatoid arthritis, lupus and multiple sclerosis; gastrointestinal disorders which include celiac disease, inflammatory bowel disease, gastrectomy and gastrointestinal by-pass procedures; endocrine/hormonal disorders which include diabetes, hyperparathyroidism, thyrotoxicosis and Cushing's syndrome; hematological disorders which include leukemia, lymphoma, multiple myeloma, sickle cell disease anemia (bone marrow disorders) and thalassemia; cancer which includes breast and prostate cancer; neurological disorders which include depression, Parkinson's disease and spinal cord injury; organ diseases which include lung (COPD, emphysema), liver and chronic kidney diseases; ankylosing spondylitis; AIDS/HIV; bone fracture; poor diet which includes eating disorders and malnutrition; and menopause (Pre-Menopause and Post-Menopause).

Historically, the osteoblast has been considered the master cell in the control of osteoclast development and, therefore, bone resorption. Now the interactions between cells of the immune system and bone cells have redefined the thinking on the regulation of bone resorption. The identification of the osteoclast and its role in bone destruction permits targeted therapy to reduce its resorptive capacity. Such therapies include the use of agents that can interfere with receptor activator of NFκB ligand (RANKL), one of the key cytokines promoting osteoclast differentiation. This may be achieved through the use of recombinant Fcosteoprotegerin (Fc-OPG) or a humanised anti-RANKL antibody (Denosumab) that is being developed by Amgen. Both products have demonstrated efficacy in preclinical models of bone loss, with Denosumab progressing through clinical trials; Fc-OPG was withdrawn from clinical trials due to immune side effects. Other inhibitors of osteoclast activity include the bisposhonates, c-src inhibitors, cathepsin K inhibitors and inhibitors of the chloride channel CLC7 (Gillespie, M. T. (2007) Arthritis Research & Therapy, Volume 9, No. 2, pp. 103-105). Notably, bisphosphonates have been successful in limiting bone loss in rodent models of arthritis, although it should be noted that the nitrogen-containing bisphosphonates (which include aldronate, ibandronate, pamidronate and zoledronate) enhance proliferation of γ/δ T lymphocytes, while non nitrogen-containing bisphosphonates (for example, clondronate) do not (Gillespie, M. T. (2007) Arthritis Research & Therapy, Volume 9, No. 2, pp. 103-105).

Most current treatment strategies attempt to reduce the bone loss of calcium in order to retard the onset of osteoporosis (Dawson-Hughes, B. et al., "A controlled trial of the effect of calcium supplementation on bone density in postmenopausal women" NEJM 323, 878-883 (1990)). As such, the most commonly used compounds for treatment of osteoporosis belong to the bisphosphonate drug class. They avidly bind to bone and are internalized by osteoclasts to inhibit bone resorption. Bisphosphonates may be administered by oral or intravenous routes. Alendronate (Fosmax™, oral) is the most commonly prescribed drug for the treatment of postmenopausal osteoporosis. Other US FDA approved bisphosphonates are Risedronate (Actonel™, oral), Etidronate (Didronel™, oral), Zoledronate (Aclasta™, infusion) and Pamidronate (Aredial™, infusion). Oral bisphosphonates are associated with gastrointestinal side effects. Side effects associated with bisphosphonates in general include unusual fractures in the femur (thigh bone) rather than at the head of the bone, which is the most common site of fracture.

However, these fractures which are associated with long-term use of bisphosphonates are rare when compared to the frequency of common hip fractures associated with osteoporosis. Nonetheless, there are concerns that long-term bisphosphonate use can result in over-suppression of bone turnover with subsequent difficulty in the healing of microcracks in the bone, propagation of these cracks and ultimately atypical fractures. Additionally, an increased risk of oesophageal cancer is associated with long-term use of oral bisphosphonates. Also, bisphosphonate use, specifically Zoledronate and Alendronate, have been reported as a risk factor for atrial fibrillation. Finally, intravenous administered bisphosphonates for the treatment of cancer have been associated with osteonecrosis of the jaw.

Parathyroid hormone (1-84 PTH) plays a central role in calcium homeostasis and, upon intermittent administration, an anabolic effect on bone remodeling. Teriparatide, approved by the US FDA (Forteo), is a recombinant form of a portion (amino acids 1-34) of PTH used for the treatment of osteoporosis in men and postmenopausal women who are at a high risk of a bone fracture. It may find some use off-label to speed healing of a bone fracture. Teriparatide enhances osteoblast formation and prevents osteoblast apoptosis. However, in spite of the anabolic effect of Teriparatide on bone, use for the treatment of osteoporosis has been guarded due to the associated high incidence of osteosarcoma in animal models. Therefore, Teriparatide is not recommended for use in patients with increased risk of bone tumors.

As a result of the potential adverse effects of long-term hormone replacement therapy (cardiovascular disorders, uterine and cancers, etc.), it is no longer recommended for the prevention of osteoporosis. As such, this has been somewhat replaced by the introduction of the Selective Estrogen Receptor Modulators (SERM) class of drugs, as exemplified by Tamoxifen and Raloxifene. Raloxifene hydrochloride was approved by the US FDA (Evista) for prevention of osteoporosis in postmenopausal women. In fact, a direct comparison with daily oral Alendronate (bisphosphonate) demonstrated that daily oral Raloxifene was equally effective at reducing the risk of bone fracture. However, side effects of Raloxifene include an increased risk of fatal stroke and venous thromboembolism. Other adverse effects include leg swelling, difficulty breathing and vision changes.

Denosumab is a fully human monoclonal antibody for the treatment of osteoporosis, treatment-induced bone loss, bone metastases, multiple myeloma and giant cell tumor of bone. Denosumab was approved by the US FDA (Prolia) for prevention of osteoporosis in postmenopausal women and (Xgeva) for the prevention of skeleton-related events in patients with bone metastases from solid tumors. This antibody binds to and inhibits RANKL (RANK ligand), a protein that acts as the primary signal for bone removal in many bone loss conditions. Osteoclast cell precursors (pre-osteoclasts) express RANK receptors. Subsequent binding of RANKL induces activation of the receptor and maturation of the pre-osteoclasts into osteoclasts. However, side effects of Denosumab include infections of the urinary and respiratory tracts, cataracts, constipation, rash and joint pain.

As may be seen from the above, multiple options are available for the prevention and/or treatment of osteoporosis but implicit with this choice is the fact that there is no universal drug available for the prevention and/or treatment of osteoporosis. As is also evident from the above, each of the cited treatment options is accompanied by multiple side effects. Indeed, the above drugs approved for human use and side effects are well documented in the scientific literature. For example, a relatively recent review article on the subject of osteoporosis and current therapies and their side effects is, "Osteoporosis—a current view of pharmacological prevention and treatment" Das, S. Crockett, J. C. Drug Design, Development and Therapy 7, 435-448 (2013). As such, a need exists for a more universal, safer (especially in view of increased longevity and hence increased duration of drug administration) drug for the prevention and/or treatment of osteoporosis. Therefore there is a need for a new treatment methods.

U.S. Pat. No. 6,372,728 (2002) assigned to AstraZeneca AB describes an improved oral formulation of bisphosphonates, e.g. Alendronate. According to this patent, the oral bioavailability of many bisphosphonates is 1%-10% between meals. The improved formulation employs a medium-chain glyceride absorption enhancer. U.S. Pat. No. 5,070,108 (1991) assigned to the University of Pennsylvania claims treatment of osteoporosis with a retinoid such as etretinate. Although initially approved by the FDA for the treatment of psoriasis, etretinate has been removed from the North American market due to the high risk of birth defects. Odanacatib is a novel drug, an inhibitor of the enzyme cathepsin K, which is under clinical development for the treatment of osteoporosis and bone metastasis.

The present invention aims to address the need for new treatment methods, compounds and pharmaceutical compositions for patients afflicted by, or susceptible to, osteoporosis.

Additional features of the invention will be apparent from a review of the discussion, figures and description of the invention herein.

BRIEF SUMMARY OF THE INVENTION

General aspects of the invention relates to the pharmaceutical use of compounds according to Formula I as defined herein, and pharmaceutically acceptable salts thereof.

Particular aspects of the invention relates to the use of compounds and compositions for the prevention and/or treatment of osteoporosis. Certain aspects concerns compounds according to Formula I as defined herein, and pharmaceutically acceptable salts thereof, as prophylactically effective and/or therapeutically effective agents against various forms of osteoporosis in subjects. According to particular embodiments, the subject is afflicted by, or susceptible to be afflicted by, bone loss, bone fracture and the like.

According to particular embodiments, the compounds and compositions of the invention are useful for stimulating bone formation and/or for stimulating bone remodeling and/or for stimulating the differentiation and mineralization of osteoblasts and/or for inhibiting bone resorption.

A particular aspect of the invention relates to a method for the prevention and/or treatment of osteoporosis, comprising the step of administering to a subject in need thereof a compound represented by Formula I, or a pharmaceutical acceptable salt thereof, as defined herein. In some embodiments, the osteoporosis is selected from the group consisting of post-menopausal osteoporosis (primary type 1), primary type 2 osteoporosis, secondary osteoporosis abnormally high osteoclastogenesis, osteomalacia-like osteoporosis, osteopenia, osteogenesis imperfecta, osteopetrosis, osteonecrosis, Paget's disease of bone, hypophosphatemia and combinations thereof. In particular embodiment the osteoporosis is post-menopausal osteoporosis (primary type 1), primary type 2 osteoporosis or secondary osteoporosis. In more specific embodiments, the osteoporosis is post-menopausal osteoporosis (primary type 1).

The invention also relates to treatment methods wherein the compounds of the invention exhibit one or more of the following biological activities in a subject: inhibition of osteoclastogenesis; stimulation of interleukin-12 (IL-12) production by a stimulated osteoclast precursor cell; reduction of acid phosphatase activity in bone cells (demonstrates a reduction in osteoclastogenesis); reduction of the Receptor activator of NF-κB ligand (RANKL) over Osteoprotegerin (OPG) ratio (RANKL/PG ratio) in bone, which indicates a reduction in osteoclastogenesis; and increase of collagen content in bone.

According to another aspect, aspect of the invention relates to a method for preventing and/or reducing bone loss, comprising the step of administering to a subject in need thereof a compound represented by Formula I or a pharmaceutical acceptable salt thereof as defined herein. In one embodiment, the administration of the compound reduces loss of calcium. In one embodiment, the subject is afflicted by or susceptible of osteoporosis. In one embodiment, the subject is a postmenopausal woman.

According to another aspect, the invention relates to a method for inhibiting osteoclastogenesis, comprising contacting an osteoclast precursor cell with a compound represented by Formula I or a pharmaceutical acceptable salt thereof as defined herein, wherein the compound inhibits differentiation of the precursor cell into an osteoclast cell.

According to another aspect, the invention relates to a method for stimulating interleukin-12 (IL-12) production by a stimulated osteoclast precursor cell, comprising contacting said stimulated osteoclast precursor cell with a compound represented by Formula I or a pharmaceutical acceptable salt thereof as defined herein, wherein an increased IL-12 production is measurable in presence of the compound.

According to another aspect, the invention relates to a method for reducing acid phosphatase activity in bone cells, comprising contacting the bone cells with a compound represented by Formula I or a pharmaceutical acceptable salt thereof as defined herein, wherein a reduced phosphatase activity is measurable in presence of the compound.

According to another aspect, the invention relates to a method for reducing expression and/or activity of receptor activator of NF-κB ligand/Osteoprotegerin ratio (RANKL/OPG ratio) in bone cells, comprising contacting the bone cells with a compound represented by Formula I or a pharmaceutical acceptable salt thereof as defined herein.

According to another aspect, the invention relates to a method for increasing collagen content in bone, comprising contacting the bone with a compound represented by Formula I or a pharmaceutical acceptable salt thereof as defined herein.

According to another aspect, the invention relates to a method for stimulating bone formation and/or for stimulating bone remodeling and/or for stimulating the differentiation and mineralization of osteoblasts and/or for inhibiting bone resorption, comprising contacting osteoblasts in said bone with a compound represented by Formula I or a pharmaceutical acceptable salt thereof as defined herein.

Additional aspects of the invention relates to the methods mentioned hereinabove, further comprising the step of administering concomitantly a drug selected from the group consisting of: bisphosphonates, Odanacatib, Alendronate, Risedronate, Etidronate, Zoledronate, Pamidronate, Teriparatide, Tamoxifen, Raloxifene, and Denosumab.

Another related aspect of the invention relates to pharmaceutical compositions comprising compounds of Formula I for the manufacture of medicaments, e.g. a medicament for the prevention and/or treatment of osteoporosis. One particular example is a pharmaceutical composition for preventing or treating osteoporosis, comprising a compound represented by Formula I as defined herein, and a pharmaceutically acceptable carrier. Another particular example is a pharmaceutical composition for preventing or treating osteoporosis, comprising a compound as defined in Table 1, and more particularly, a pharmaceutical composition comprising Compound I. Related aspect concerns methods for the prevention and/or treatment of osteoporosis, comprising administering to a patient a therapeutically effective amount of a pharmaceutical composition as defined herein.

According to another aspect, the invention relates to a compound represented by Formula I or a pharmaceutical acceptable salt thereof as defined herein or to a composition comprising the same, for use in the prevention and/or treatment of osteoporosis.

Further aspects of the invention will be apparent to a person skilled in the art from the following description, claims, and generalizations herein.

DETAILED DESCRIPTION OF THE INVENTION

Figure 1:
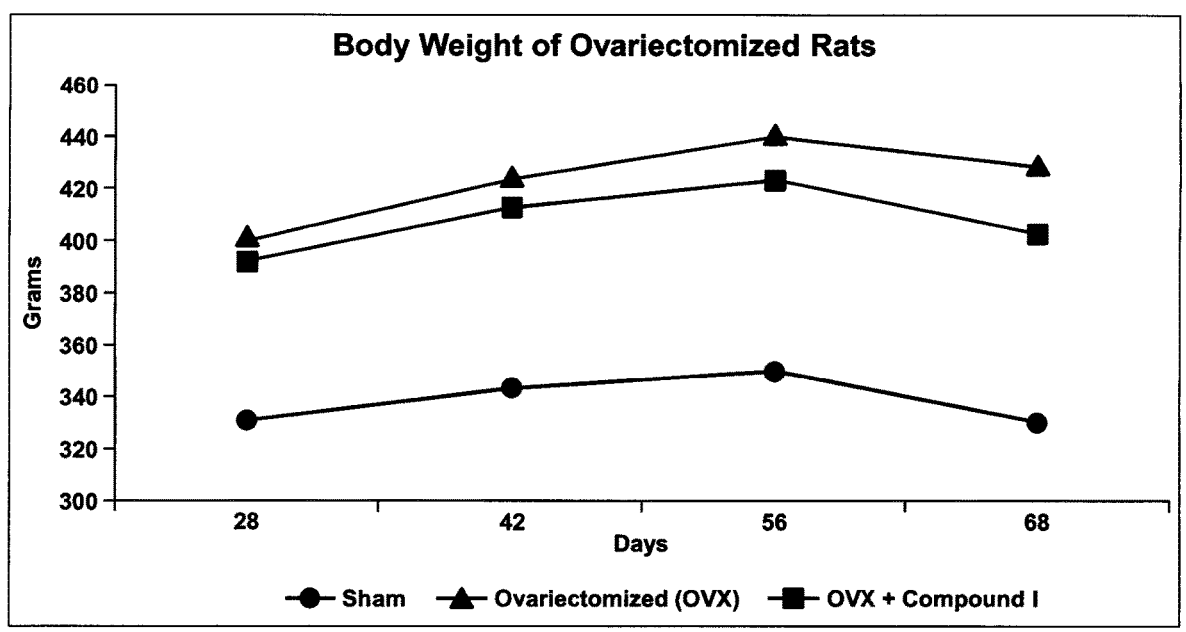
FIG. 1 is a line graph demonstrating the effect of Compound I on body weight of ovariectomized (OVX) rats, according to Example 3.

The present discloses compounds of Formula I, pharmaceutically acceptable salts thereof, compositions comprising same and uses thereof. Various embodiments of the present invention include:

A) Compounds of the Invention

According to one aspect, the invention concerns the pharmaceutical uses of compounds represented by Formula I, or pharmaceutically acceptable salts thereof:

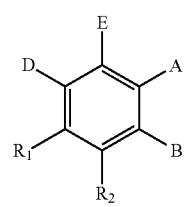

Formula I wherein:
$R_1$ and $R_2$ are independently equal to H, F or OH;
A is $(CH_2)_m COOH$, $W(CH_2)_m COOH$ or

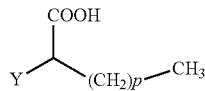

when B is H; or B is $(CH_2)_m COOH$, $W(CH_2)_m COOH$ or

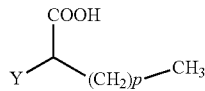

when A is H; or
A and B are covalently bonded to form a five (5), six (6) or seven (7)-membered cycloalkyl substituted with COOH;
where:
Y is O, S, NH, or $CH_2$;
W is O, S, or NH;
m is 0-2; and
p is 3-7;
D is $CO(CH_2)_n CH_3$ or $CHOH(CH_2)_n CH_3$ or $O(CH_2)_n CH_3$ where n is 2-6; and
E is H or F.

According to a particular embodiment, A is $(CH_2)_m COOH$, $W(CH_2)_m COOH$ or

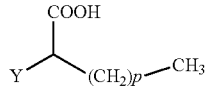

when B is H; or B is $(CH_2)_m COOH$, $W(CH_2)_m COOH$ or

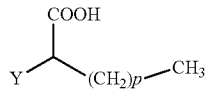

when A is H; and A and B are not covalently bonded together to form a cycloalkyl substituted with COOH.

According to a particular embodiment, A is

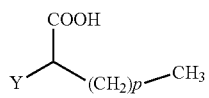

when B is H; or B is

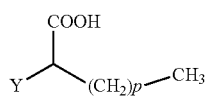

when A is H; or A and B are covalently bonded together to form a five (5), six (6) or seven (7)-membered cycloalkyl substituted with COOH.

According to a particular embodiment, n is 3-6, or n is 4-6, or n is 6.

According to a particular embodiment, $R_1$ is H and $R_2$ is H.

According to a particular embodiment, A is H and B is

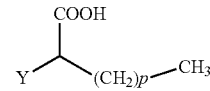

wherein Y is O, and p is 5-7, and preferably p is 7.

According to a particular embodiment, m is 1-2; and preferably m is 1 or preferably m is 2.

According to a particular embodiment, E is H; and D is $CO(CH_2)_n CH_3$ or $CHOH(CH_2)_n CH_3$ or $O(CH_2)_n CH_3$ where n is 2-6, or n is 4-6.

According to a particular embodiment, D is $CO(CH_2)_n CH_3$ where n is 2-6, or n is 4-6.

According to a particular embodiment, E is H; and D is $CO(CH_2)_n CH_3$ where n is 2-6, or n is 4-6.

According to a particular embodiment, the compound is of Formula I; wherein $R_1$ and $R_2$ are H; A is H; B is

where Y is O, and p is 5-7; E is H; D is $CO(CH_2)_n CH_3$ or $CHOH(CH_2)_n CH_3$ or $O(CH_2)_n CH_3$; and n is 2-6, or n is 4-6.

According to a particular embodiment, the compound is of Formula I wherein $R_1$ and $R_2$ are H; A is H; B is

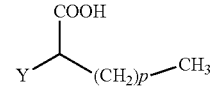

where Y is O and p is 5-7; E is H; D is $CO(CH_2)_n CH_3$; and n is 2-6, or n is 4-6.

According to a particular embodiment, the compound is of Formula I wherein n is 4-6; $R_1$ and $R_2$ are H; B is H; A is

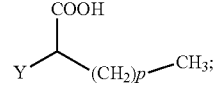

Y is O; and p is 5-7; E is H; D is $CO(CH_2)_n CH_3$ or $CHOH(CH_2)_n CH_3$ or $O(CH_2)_n CH_3$; and n is 2-6, or n is 4-6.

As used herein, the term "cycloalkyl" is intended to mean a monocyclic saturated aliphatic hydrocarbon group having the specified number of carbon atoms therein, for example, as in $C_5$-$C_7$ cycloalkyl is defined as including groups having 5, 6 or 7 carbons in a monocyclic arrangement. Examples of $C_5$-$C_7$ cycloalkyl include, but are not limited to, cyclopentyl, cyclohexyl and cycloheptyl.

Examples of compounds of Formula I include, but are not limited to, Compounds I to VII listed in Table 1 hereinafter. In a preferred embodiment, the compound is represented by the acid form or a pharmaceutically acceptable salt of any one of Compounds I to VII.

The Applicants have described elsewhere compounds whose structure is related to the structure of some of the compounds of the present invention. Reference is made for instance to the compounds disclosed international PCT application WO 2012/055014 which is incorporated herein by reference in its entirety. Accordingly, in particular embodiments any one or all the Compounds disclosed this PCT is excluded from the scope of the present invention.

Salts

As used herein, the term "pharmaceutically acceptable salt" is intended to mean base addition salts. Example of pharmaceutically acceptable salts are also described, for example, in Berge et al., "Pharmaceutical Salts", *J. Pharm. Sci* 66, 1-19 (1977). Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

The pharmaceutically acceptable salt of the compounds of Formula I may be selected from the group consisting of base addition salts of sodium, potassium, calcium, magnesium and lithium, ammonium, manganese, zinc, iron, or copper. In preferred embodiments, the pharmaceutically acceptable salt of the compounds according to the invention may be the sodium, potassium, calcium, magnesium or lithium salt. More preferably the pharmaceutically acceptable salt is sodium.

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

Prodrugs

In certain embodiments, the compounds of the present invention as represented by generalized Formula I, wherein said compounds are present in the free carboxylic acid form, may also include all pharmaceutically acceptable salts, isosteric equivalents such as tetrazole and prodrug forms thereof. Examples of the latter include the pharmaceutically acceptable esters or amides obtained upon reaction of alcohols or amines, including amino acids, with the free acids defined by Formula I.

Chirality

The compounds of the present invention, their pharmaceutically acceptable salts, or prodrugs thereof, may contain one or more asymmetric centers, chiral axes and chiral planes and may thus give rise to enantiomers, diastereomers, and other stereoisomeric forms and may be defined in terms of absolute stereochemistry, such as (R)- or (S)-. The present invention is intended to include all such possible isomers, as well as, their racemic and optically pure forms. Optically active (+) and (−), (R)- and (S)-, isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Hydrates

In addition, the compounds of the invention also may exist in hydrated and anhydrous forms. Hydrates of any of the formulas described herein are included as compounds of the invention which may exist as a monohydrate or in the form of a polyhydrate.

B) Methods of Preparation

In general, all compounds of the present invention may be prepared by any conventional methods, using readily available and/or conventionally preparable starting materials, reagents and conventional synthesis procedures. Of particular interest is the work of Hundertmark, T.; Littke, A. F.; Buchwald, S. L.; Fu, G. C. Org. Lett. 12, 1729-1731 (2000).

The exemplification section hereinafter provides general schemes and specific, but non limitative, examples for the synthesis of Compounds I to VII.

C) Pharmaceutical Applications

As indicated and exemplified herein, the compounds of the present invention have beneficial pharmaceutical properties and these compounds may have useful pharmaceutical applications in subjects. Medical and pharmaceutical applications contemplated by the inventors include, but are not limited to, prevention and/or treatment of various forms of osteoporosis. As used herein, the term "osteoporosis" refers to a progressive bone disease that is characterized by a decrease in bone mass and density which can lead to an increased risk of bone fracture. The term "osteoporosis" encompasses primary type 1 osteoporosis or postmenopausal osteoporosis (most common in women after menopause), primary type 2 osteoporosis (occurs in both females and males generally after age 75), and secondary osteoporosis (which may arise at any age, a form that results from chronic predisposing medical problems or disease, or prolonged use of medications such as glucocorticoids (the disease may then be called steroid- or glucocorticoid-induced osteoporosis)). As used herein, "osteoporosis" also include bone disorders involving a loss in bone mass and/or density such as abnormally high osteoclastogenesis, osteomalacia-like osteoporosis, osteopenia, osteogenesis imperfecta, osteopetrosis, osteonecrosis, Paget's disease of bone, hypophosphatemia and combinations thereof.

As is known, various diseases and conditions may cause osteoporosis, and the present invention may be useful in preventing and/or treating osteoporosis related, directly or indirectly to one or more of these causes:

Autoimmune diseases which include rheumatoid arthritis, lupus and multiple sclerosis;

Gastrointestinal disorders which include celiac disease, inflammatory bowel disease, gastrectomy and gastrointestinal by-pass procedures;

Endocrine/Hormonal disorders which include diabetes, hyperparathyroidism, thyrotoxicosis and Cushing's syndrome;

Hematological disorders which include leukemia, lymphoma, multiple myeloma, sickle cell disease anemia (bone marrow disorders) and thalassemia;

Cancer which include breast and prostate cancer;

Neurological disorders which include depression, Parkinson's disease and spinal cord injury;

Organ diseases which include lung (COPD, emphysema), liver and chronic kidney diseases (CKD);

Ankylosing spondylitis;

AIDS/HIV;

Poor diet which include eating disorders and malnutrition; and

Peri- or postmenopausal osteoporosis and corticosteroid induced osteoporosis.

In one embodiment the osteoporosis is primary type 1 osteoporosis or postmenopausal osteoporosis. In another embodiment the osteoporosis is primary type 2 osteoporosis.

The term "subject" includes living organisms in which osteoporosis can occur, or which are susceptible to such disease. The term "subject" includes animals such as mammals or birds. Preferably, the subject is a mammal. More preferably, the subject is a human. Most preferably, the subject is a human patient in need of treatment. In preferred embodiments, the subject is a person having or suffering from any of the following conditions: primary type 1 osteoporosis, postmenopausal osteoporosis, menopause (pre-menopause and post-menopause), primary type 2 osteoporosis, more than 75 years old, bone fracture, osteoporosis, chronic predisposing medical problems or disease, prolonged use of medications such as glucocorticoids, abnormally high osteoclastogenesis, osteomalacia-like osteoporosis, osteopenia, osteogenesis imperfecta, osteopetrosis, osteonecrosis, Paget's disease of bone, hypophosphatemia and combinations thereof. In a preferred embodiment, the subject is a postmenopausal women.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians. In preferred embodiments, "preventing" or "prevention" refers to preventing decrease in bone mass and/or bone density, and/or to reducing risk of bone fracture.

The terms "treatment" or "treating" of a subject includes the application or administration of a compound of the invention to a subject (or application or administration of a compound of the invention to a cell or tissue from a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required. In preferred embodiments, "treatment" or "treating" refers to increasing bone mass and/or bone density, and/or increasing healing of bone fracture.

Furthermore, in some embodiments the compounds of the invention are for used monotherapy for the treatment prevention and/or treatment of osteoporosis. In other embodiments, the compounds of the invention are used in combination with already approved drugs, including but not limited to drugs used for the treatment of osteoporosis. Examples of known osteoporosis-related agents which may be used in combination with the compounds of the present invention include, but are not limited to bisphosphonates, Odanacatib, Alendronate, Risedronate, Etidronate, Zoledronate, Pamidronate, Teriparatide, Tamoxifen, Raloxifene, and Denosumab.

Accordingly, methods of treatment according to the present invention may also include co-administration of the at least one compound according to the invention, or a pharmaceutically acceptable salt thereof, together with the administration of another therapeutically effective agent. Therefore, an additional aspect of the invention relates to methods of concomitant therapeutic treatment of a subject, comprising administering to a subject in need thereof an effective amount of a first agent and a second agent, wherein the first agent is as defined in Formula I, and the second agent is for the prevention or treatment of any one of disorder or disease as defined hereinbefore. As used herein, the term "concomitant" or "concomitantly" as in the phrases "concomitant therapeutic treatment" or "concomitantly with" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g., a human).

Accordingly, the invention also relates to a method for preventing, reducing or eliminating a symptom or complication of any one of the above mentioned diseases or conditions. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I as defined herein, or a pharmaceutically acceptable salt thereof, e.g., sodium salt. The second agent may be selected from the list of compounds given hereinbefore (e.g. agents or drugs used for the prevention and/or treatment of osteoporosis).

Inhibition of Osteoclastogenesis

Osteoclasts are a type of bone cell that resorbs bone tissue. The osteoclast disassembles the bone at a molecular level by secreting acid and a collagenase. This process is known as bone resorption. Osteoclastogenesis refers to the differentiation of precursor of osteoclasts into osteoclasts. In the prevention and/or treatment of osteoporosis, it is desirable to reduce osteoclastogenesis.

Osteoblast is a type of cells that synthesizes bone. Osteoblasts arise from mesenchymal stem cells. In the prevention and/or treatment of osteoporosis, it is desirable is to stimulate osteoblastic differentiation.

As shown hereinafter in the examples, the compounds of the invention are capable of inhibiting and/or reducing osteoclastogenesis. This is demonstrated for example by: a strong induction of IL-12 production in LPS-stimulated RAW264.7 cells (Example 3, Table 1); a reduction of calcium loss in vivo (Example 4, FIG. 2); a reduction of acid phosphatase activity in vivo (Example 4, FIG. 3); a decrease of mRNA expression of RANKL/OPG in vivo (Example 4, FIG. 4); and an increase collagen content in vivo (Example 4, FIGS. 5, 6 and 7).

These results suggest an ability of the compounds of the present invention to prevent/treat osteoporosis, via the inhibition and/or reduction of activity of osteoclasts.

The results also demonstrate an ability of the compounds of the present invention to prevent and/or reduce bone loss, including but not limited to, calcium loss. Accordingly, these results further suggest an ability of the compounds of the present invention to prevent/treat osteoporosis, via the stimulation of osteoblastic differentiation.

Stimulation of Interleukin-12 (IL-12) Production

As shown hereinafter in the examples, the compounds of the invention induce the production of IL-12 in the presence of LPS. These results suggest an ability of these compounds to prevent and/or treat osteoporosis, as a result of the induction of IL-12. This is supported by the scientific literature that teaches that IL-12 has a direct inhibitory effect on osteoclastogenesis.

Accordingly, in some embodiments, the compounds and compositions of the invention are useful for the stimulation of interleukin-12 (IL-12) production including, but not limited to, production by a stimulated osteoclast precursor cell.

Reduction of Acid Phosphatase Activity

As shown hereinafter in the examples, the compounds of the invention reduce enzymatic acid phosphatase activity, as measured in the serum of ovariectomized rats. These results suggest an ability of these compounds to prevent and/or treat osteoporosis as a result of reduction of enzymatic acid phosphatase activity.

Accordingly, in some embodiments, the compounds and compositions of the invention are useful for reducing acid phosphatase activity in bone cells.

Reducing Expression of Receptor Activator of NF-κB Ligand (RANKL)

As shown hereinafter in the examples, the compounds of the invention reduce mRNA expression of RANKL, as measured in the tibia of ovariectomized rats. These results suggest an ability of these compounds to prevent and/or treat osteoporosis as a result of reduction of RANKL's expression and/or biological activity.

Accordingly, in some embodiments, the compounds and compositions of the invention are useful for reducing expression and/or activity of RANKL in bone cells.

Increasing Collagen Content

As shown hereinafter in the examples, the compounds of the invention increase the content of collagen in bone, as measured in the metaphyse of the femur of ovariectomized rats. These results suggest an ability of these compounds to prevent and/or treat osteoporosis as demonstrated by the increase of the collagen content in the bone.

Accordingly, in some embodiments, the compounds and compositions of the invention are useful for increasing collagen content in living bone.

Stimulating Bone Formation

In some embodiments, the compounds and compositions of the invention are useful for stimulating bone formation and/or for stimulating bone remodeling and/or for stimulating the differentiation and mineralization of osteoblasts and/or for inhibiting bone resorption.

D) Pharmaceutical Compositions and Formulations

A related aspect of the invention concerns pharmaceutical compositions comprising a therapeutically effective amount one or more of the compounds of the invention described herein (e.g., a compound of Formula I). As indicated hereinbefore, the pharmaceutical compositions of the invention may be useful: in the prevention and/or treatment of osteoporosis; in the inhibition of osteoclastogenesis; in stimulating interleukin-12 (IL-12) production by a stimulated osteoclast precursor cell; in the reduction of acid phosphatase activity in bone cells; in the reduction of expression of Receptor activator of NF-κB ligand (RANKL) in bone cells; in increasing collagen content in living bone, in stimulating bone formation; in stimulating bone remodeling; in stimulating bone mineralization; and/or in inhibiting bone resorption.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject (e.g., total or partial response as evidenced by factors which include increasing bone mass and/or bone density (or reduction of a decrease thereof), reducing a risk of bone fracture, etc.), the properties of the compounds (e.g., bioavailability, stability, potency, toxicity, etc.), and the particular disorder(s) the subject is suffering from. In addition, the therapeutically effective amount may depend on the subject's blood parameters (e.g., calcium levels, lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained. The dose to be administered will ultimately be at the discretion of the oncologist. In general, however, it is envisioned that the dose for the present compounds may be in the range of about 1 to about 50 mg/kg per day in human. In selected embodiments, the range may be between 1 to 30 mg/kg per day in human. In selected embodiments, the range may be between 1 to 20 mg/kg per day in human. In selected embodiments, the range may be between 5 to 18 mg/kg per day in human. In selected embodiments, the range may be between 1 to 18 mg/kg per day in human.

As used herein, the term "pharmaceutical composition" refers to the presence of at least one compound of the invention according to Formula I as defined herein and at least one pharmaceutically acceptable carrier, diluent, vehicle or excipient. As used herein, the term "pharmaceutically acceptable carrier", "pharmaceutically acceptable diluent" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

The composition of the present invention may include one or more compounds of Formula I as defined herein or pharmaceutically acceptable derivatives, salts prodrugs, analogues and isomers or enantiomers thereof. Formulations of the active compound may be prepared so as to provide a pharmaceutical composition in a form suitable for enteral, mucosal (including sublingual, pulmonary and rectal), parenteral (including intramuscular, intradermal, subcutaneous and intravenous) or topical (including ointments, creams or lotions) administration. The formulation may, where appropriate, be conveniently presented in discrete dosage units and may be prepared by any of the methods well-known in the art of pharmaceutical formulation. All methods include the step of bringing together the active pharmaceutical ingredient with liquid carriers or finely divided solid carriers or both as the need dictates. When appropriate, the above-described formulations may be adapted so as to provide sustained release of the active pharmaceutical ingredient. Sustained release formulations well-known to the art include the use of a bolus injection, continuous infusion, biocompatible polymers or liposomes.

E) Kits

The compound(s) of the invention may be packaged as part of a kit, optionally including a container (e.g., packaging, a box, a vial, etc.). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of at least one compound according to the invention as defined by Formula I as defined herein, or a pharmaceutically acceptable salt thereof, and a unit dosage form of at least one additional active ingredient. Examples of additional active ingredients that may be used in conjunction with the compounds of the invention include, but are not limited to, any of the drugs indicated hereinbefore (e.g. drugs used for the treatment of osteoporosis) that could be used in combination with the compound(s) of the invention.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

EXAMPLES

The following examples further illustrate the practice of this invention but are not intended to be limiting thereof.

Example 1: Experimental Procedures for the Preparation Certain Representative Compounds All HPLC chromatograms and mass spectra were recorded on an HP 1100 LC-MS Agilent™ instrument using an analytical C18 column (250×4.6 mm, 5 microns) with a gradient over 5 min of 15-99% $CH_3CN$—$H_2O$ with 0.01% TFA as the eluent and a flow of 2 mL/min.

Compound I: Sodium (RS)-2-[4-Octanoylphenoxy]decanoate

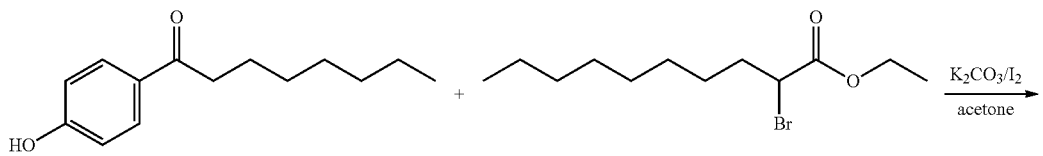

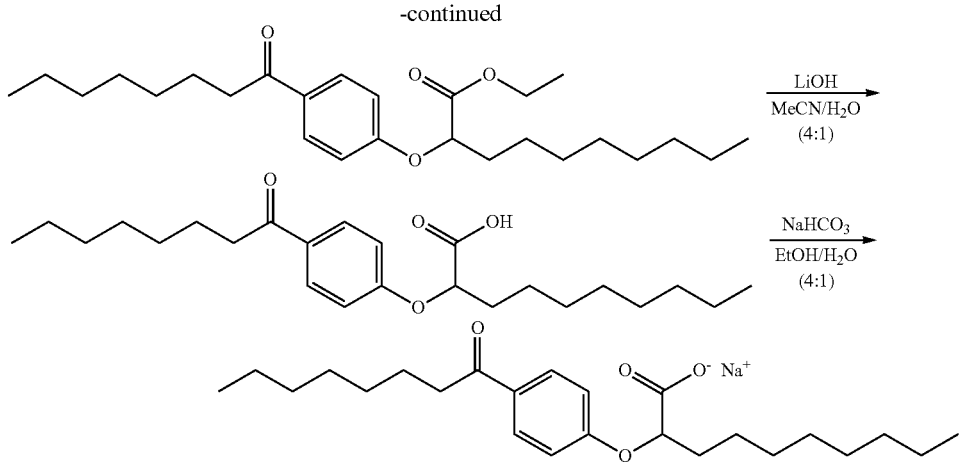

A mixture of 1-[4-hydroxyphenyl]octan-1-one (10.0 g, 45.4 mmol), $K_2CO_3$ (9.4 g, 68.1 mmol) and iodine (1.5 g, 9.1 mmol) in acetone (100 mL), was treated with ethyl 2-bromodecanoate (13.9 g, 49.9 mmol), and the reaction was stirred at room temperature, under nitrogen, overnight. Solvent was evaporated in vacuo, and the residue was partitioned between ethyl acetate and water. The organic phase was washed with saturated aqueous sodium chloride, dried over magnesium sulfate, filtered and evaporated in vacuo. The crude material was purified on a silica gel pad, eluting with 5% ethyl acetate/hexane to give ethyl (RS)-2-[4-octanoylphenoxy]decanoate (11.9 g, 62%) as a colorless oil. $^1$H NMR (400 MHz, $CDCl_3$): δ 7.92 (d, J=9.0 Hz, 2H), 6.89 (d, J=9.0 Hz, 2H), 4.66 (dd, J=7.5, 5.2 Hz, 1H), 4.21 (q, J=7.0 Hz, 2H), 2.89 (t, J=7.4 Hz, 2H), 1.90-2.03 (m, 2H), 1.66-1.74 (m, 2H), 1.43-1.56 (m, 2H), 1.24-1.37 (m, 18H), 1.24 (t, J=7.2 Hz, 2H), 0.85-0.89 (m, 6H). A solution of ethyl ester (11.9 g, 28.3 mmol) in a mixture of tetrahydrofuran (360 mL), methanol (90 mL) and water (90 mL), was treated with lithium hydroxide monohydrate (5.9 g, 141.5 mmol), and the mixture was stirred at room temperature for 20 h. A second portion of lithium hydroxide monohydrate (2.3 g, 54.8 mmol) was added and the reaction was stirred at room temperature for an additional 3 h. The reaction mixture was concentrated in vacuo and the residue was partitioned between ethyl acetate and water. The organic phase was washed with saturated aqueous sodium chloride, dried over magnesium sulfate, filtered and evaporated in vacuo, to give the crude product. Purification on a silica gel pad, eluting with 40% ethyl acetate/hexane; and recrystallization from hexanes gave (RS)-2-[4-octanoylphenoxy]decanoic acid (9.46 g, 86%) as a white solid. m.p. 45-47° C.; $^1$H NMR (400 MHz, $CDCl_3$): δ 7.93 (d, J=9.0 Hz, 2H), 6.91 (d, J=9.0 Hz, 2H), 4.72 (dd, J=6.8, 5.7 Hz, 1H), 2.90 (t, J=7.4 Hz, 2H), 1.98-2.04 (m, 2H), 1.67-1.74 (m, 2H), 1.46-1.59 (m, 2H), 1.24-1.37 (m, 18H), 0.87 (t, J=6.9 Hz, 3H), 0.88 (t, J=6.9 Hz, 3H). A solution of the acid (9.4 g, 24.1 mmol) in ethanol (200 mL) was treated with a solution of sodium bicarbonate (2.0 g, 24.1 mmol) in water (50 mL), and the reaction was stirred at room temperature for 5 h. Solvents were concentrated in vacuo, and the solution was diluted with water (950 mL), filtered (0.2 μm), and lyophilised to give sodium (RS)-2-[4-octanoylphenoxy]decanoate as a white solid (8.8 g, 88%). mp 275-280° C.; $^1$H NMR (400 MHz, $CD_3OD$): δ 7.96 (d, J=9.0 Hz, 2H), 6.97 (d, J=9.0 Hz, 2H), 4.72 (dd, J=6.2, 5.9 Hz, 1H), 2.95 (t, J=7.4 Hz, 2H), 1.94-1.99 (m, 2H), 1.64-1.72 (m, 2H), 1.49-1.57 (m, 2H), 1.28-1.40 (m, 18H), 0.90 (t, J=6.9 Hz, 3H), 0.89 (t, J=6.9 Hz, 3H); $^{13}$C NMR (101 MHz, $CD_3OD$): δ 200.72, 177.83, 163.37, 130.20, 129.61, 114.70, 79.55, 37.94, 33.19, 31.87, 31.76, 29.45, 29.38, 29.24, 29.22, 29.16, 25.74, 24.85, 22.57, 22.52, 13.29, 13.28; LRMS (ESI): m/z 391 (M-$Na^+$+2$H^+$); HPLC: 6 min.

Resolution of Compound I Through a Chiral Ester Auxiliary:

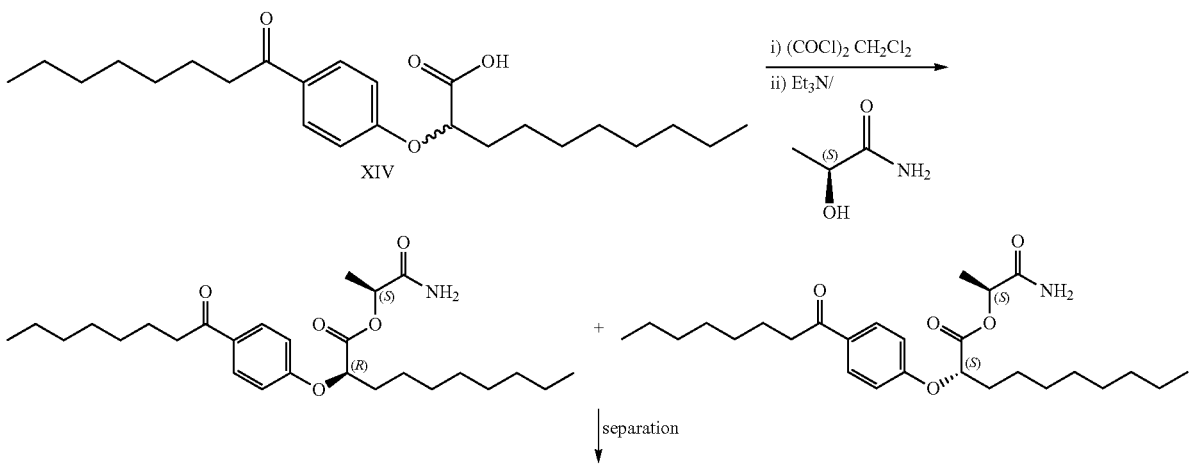

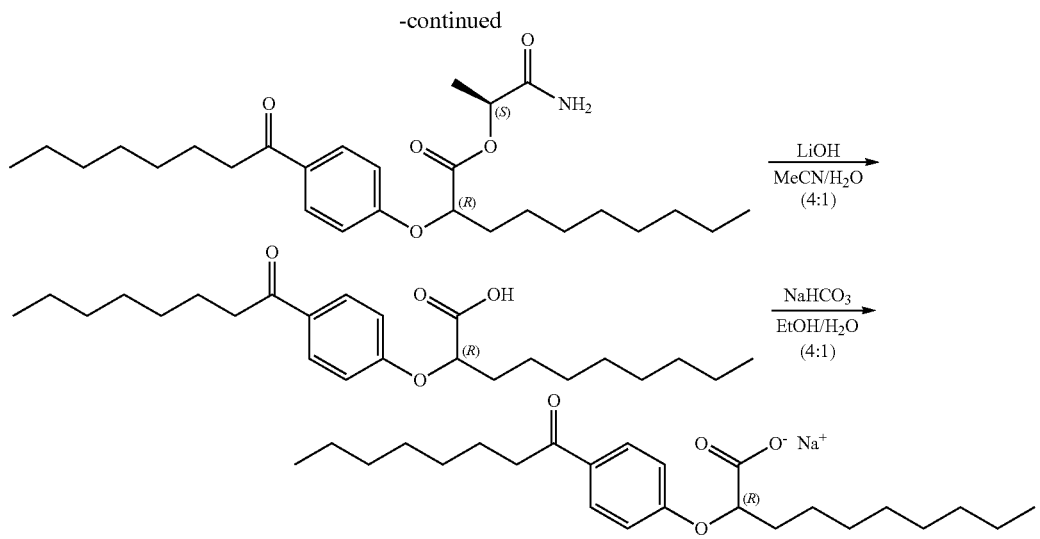

The same procedure was repeated for the (S) isomer

Sodium Salts of (R)- & (S)-2-[4-Octanoylphenoxy]decanoate

1. Formation and Separation of (S)-Lactamide Esters:

A solution of (RS)-2-[4-octanoylphenoxy]decanoic acid (0.95 g, 2.4 mmol) in dichloromethane (20 mL) was treated dropwise with oxalyl chloride (0.26 mL, 3.1 mmol), and the reaction was stirred at room temperature for 1 hour. triethylamine (0.51 mL, 3.7 mmol) was added, followed by (S)-lactamide (0.54 g, 6.1 mmol), and the reaction was stirred at room temperature for 20 hours. The solution was then diluted with ethyl acetate (100 mL), and washed with 1M aqueous HCl (100 mL), water (100 mL) and saturated aqueous sodium chloride (50 mL), then dried over sodium sulphate and evaporated in vacuo. The two diastereomers were separated on a Biotage™ 40 L column (silica), eluted with diethyl ether/hexane 1:4 to 1:1, then with ethyl acetate/hexane 1:4 to 1:1. This gives the separate pure diastereomers.

First diastereomer (0.51 g, 45%) as a white, waxy solid: $^1$H NMR (400 MHz, CDCl$_3$): δ 7.93 (d, J=9.0 Hz, 2H), 6.91 (d, J=8.8 Hz, 2H), 5.68 (br s, 1H), 5.54 (br s, 1H), 5.22 (q, J=6.8 Hz, 1H), 4.77 (dd, J=7.3, 5.2 Hz, 1H), 2.88 (t, J=7.5 Hz, 2H), 1.92-2.08 (m, 2H), 1.69, (tt, J=7.3, 7.3 Hz, 2H), 1.46-1.56 (m, 2H), 1.47, (d, J=6.8 Hz, 3H), 1.23-1.38 (m, 18H), 0.86 (t, J=6.6 Hz, 6H); $^{13}$C NMR (101 MHz, CDCl$_3$): δ 199.15, 172.34, 170.09, 161.35, 131.47, 130.82, 114.56, 76.70, 71.16, 38.59, 32.90, 32.00, 31.93, 29.57, 29.52, 29.35 (3C), 25.26, 24.68, 22.84 (2C), 17.85, 14.29 (2C).

Second diastereomer (0.47 g, 42%) as a viscous, colourless oil: $^1$H NMR (400 MHz, CDCl$_3$): δ 7.90 (d, J=9.0 Hz, 2H), 6.91 (d, J=9.0 Hz, 2H), 6.25 (br s, 1H), 6.15 (br s, 1H), 5.20 (q, J=6.9 Hz, 1H), 4.79 (dd, J=6.6, 5.9 Hz, 1H), 2.88 (t, J=7.5 Hz, 2H), 1.95-2.01 (m, 2H), 1.68, (tt, J=7.3, 7.3 Hz, 2H), 1.47-1.55 (m, 2H), 1.39, (d, J=6.8 Hz, 3H), 1.22-1.37 (m, 18H), 0.86 (t, J=6.8 Hz, 6H); $^{13}$C NMR (101 MHz, CDCl$_3$): δ 199.43, 172.71, 170.29, 161.52, 131.31, 130.60, 114.84, 76.48, 71.13, 38.59, 32.80, 32.00, 31.93, 29.58, 29.53, 29.36 (3C), 25.36, 24.76, 22.84, 17.69, 14.29 (2C).

2. Conversion of Diastereomers to the Corresponding Sodium Salt:

General Procedure:

A solution of diastereomeric ester (1.73 g, 3.7 mmol) in acetonitrile (72 mL) was treated with a solution of lithium hydroxide (0.45 g, 18.7 mmol) in water (18 mL), and the reaction was stirred at room temperature for 17 hours. The reaction was quenched by addition of 1M aqueous HCl (150 mL), and extracted with ethyl acetate (2×100 mL). Combined extracts were washed with water (150 mL) and saturated aqueous sodium chloride (150 mL); then dried over sodium sulfate, filtered and evaporated in vacuo to give the crude acid.

First Enantiomer (higher R$_f$, silica gel): Purification on a Biotage™ 40 L column (silica), eluted with ethyl acetate/hexane 1:9 to 7:3, gave the purified acid enantiomer as a white solid (1.28 g, 87%). $^1$H NMR (400 MHz, CDCl$_3$): δ 11.50 (s, 1H), 7.92 (d, J=8.8 Hz, 2H), 6.90 (d, J=9.0 Hz, 2H), 4.71 (dd, J=6.4, 5.9 Hz, 1H), 2.89 (t, J=7.4 Hz, 2H), 1.97-2.03 (m, 2H), 1.69, (tt, J=7.1, 7.1 Hz, 2H), 1.45-1.59 (m, 2H), 1.21-1.38 (m, 18H), 0.862 (t, J=7.0 Hz, 3H), 0.859 (t, J=6.8 Hz, 3H); $^{13}$C NMR (101 MHz, CDCl$_3$): δ 200.20, 176.59, 161.76, 131.00, 130.77, 114.83, 76.15, 38.59, 32.80, 32.03, 31.93, 29.59, 29.53, 29.39, 29.37 (2C), 25.38, 24.91, 22.89 (2C), 14.30 (2C).

A solution of the acid (1.28 g, 3.2 mmol) in ethanol (20 mL) was treated with a solution of sodium bicarbonate (0.27 g, 3.2 mmol) in water (5 mL), and the reaction was stirred at room temperature for 3 days. Solvents were evaporated in vacuo to give the crude salt as a white waxy solid. This material was dissolved in water (130 mL), filtered (0.2 micron; nylon) and lyophilised to give the pure enantiomer as a white solid (1.1 g, 97%). $^1$H NMR (400 MHz, CD$_3$OD): δ 7.91 (d, J=8.6 Hz, 2H), 6.96 (d, J=8.8 Hz, 2H), 4.46 (t, J=6.2 Hz, 1H), 2.92 (t, J=7.3 Hz, 2H), 1.90-1.95 (m, 2H), 1.66, (tt, J=7.2, 7.2 Hz, 2H), 1.44-1.61 (m, 2H), 1.24-1.39 (m, 18H), 0.890 (t, J=6.7 Hz, 3H), 0.882 (t, J=6.7 Hz, 3H); $^{13}$C NMR (101 MHz, CD$_3$OD): δ 200.66, 177.83, 163.37, 130.24, 129.64, 114.73, 79.59, 37.96, 33.20, 31.87, 31.76, 29.46, 29.40, 29.26, 29.22, 29.16, 25.75, 24.86, 22.57, 22.53, 13.32, 13.29; other data to be collected.

Second enantiomer (lower R$_f$, silica gel): Purification on a Biotage™ 40 L column (silica), eluted with ethyl acetate/hexane 1:9 to 7:3, gave the purified acid enantiomer as a white solid (1.10 g, 87%). ¹H NMR (400 MHz, CDCl₃): δ 11.51 (s, 1H), 7.91 (d, J=9.0 Hz, 2H), 6.90 (d, J=9.0 Hz, 2H), 4.71 (dd, J=6.6, 5.9 Hz, 1H), 2.89 (t, J=7.5 Hz, 2H), 1.97-2.03 (m, 2H), 1.69, (tt, J=7.1, 7.1 Hz, 2H), 1.45-1.58 (m, 2H), 1.21-1.37 (m, 18H), 0.862 (t, J=7.0 Hz, 3H), 0.858 (t, J=7.0 Hz, 3H); ¹³C NMR (101 MHz, CDCl₃): δ 200.16, 176.47, 161.77, 131.03, 130.76, 114.84, 76.18, 38.58, 32.79, 32.02, 31.93, 29.58, 29.52, 29.37, 29.36 (2C), 25.36, 24.91, 22.84 (2C), 14.35, 14.28.

A solution of the acid (1.1 g, 2.7 mmol) in ethanol (16 mL) was treated with a solution of sodium bicarbonate (0.23 g, 2.7 mmol) in water (4 mL), and the reaction was stirred at ambient temperature for 18 h. Solvents were evaporated in vacuo to give the crude salt as a clear, colourless syrup. This material was dissolved in water (100 mL), filtered (0.2 micron; nylon) and lyophilised to give the pure enantiomer as a white solid (1.12 g, 99%). ¹H NMR (400 MHz, CD₃OD): δ 7.91 (d, J=9.0 Hz, 2H), 6.96 (d, J=9.0 Hz, 2H), 4.46 (t, J=6.2 Hz, 1H), 2.92 (t, J=7.4 Hz, 2H), 1.90-1.95 (m, 2H), 1.66, (tt, J=7.1, 7.1 Hz, 2H), 1.45-1.61 (m, 2H), 1.24-1.39 (m, 18H), 0.890 (t, J=6.8 Hz, 3H), 0.881 (t, J=6.9 Hz, 3H); ¹³C NMR (101 MHz, CD₃OD): δ 200.65, 177.82, 163.37, 130.20, 129.65, 114.74, 79.58, 37.96, 33.19, 31.87, 31.76, 29.46, 29.40, 29.26, 29.22, 29.16, 25.75, 24.86, 22.57, 22.53, 13.32, 13.29.

Compound II: Sodium (RS)-2-[3-Fluoro-4-octanoylphenoxy]decanoate

The title compound was prepared using the same procedure as for Compound I starting from 3-fluoro-4-octanoylphenol (prepared by Friedel-Crafts acylation of 3-fluorophenol). mp 220-226° C.; ¹H NMR (400 MHz, CD₃OD): δ 7.78 (dd, $J_{HH}$=8.8 Hz, $J_{HF}$=8.8 Hz, 1H), 6.79 (dd, $J_{HH}$=8.8 Hz, 2.3 Hz, 1H), 6.67 (dd, $J_{HF}$=13.7 Hz, $J_{HH}$=2.3 Hz, 1H), 4.44 (t, J=6.3 Hz, 1H), 2.89 (td, $J_{HH}$=7.3 Hz, $J_{HF}$=2.7 Hz, 2H), 1.89-1.94 (m, 2H), 1.61-1.66 (m, 2H), 1.44-1.60 (m, 2H), 1.24-1.38 (m, 18H), 0.89 (t, J=6.9 Hz, 3H), 0.88 (t, J=6.9 Hz, 3H); ¹³C NMR (101 MHz, CD₃OD): δ 198.20 (d, $J_{CF}$=4.6 Hz), 177.23, 164.63 (d, $J_{CF}$=12.3 Hz), 163.62 (d, $J_{CF}$=253.7 Hz), 131.60 (d, $J_{CF}$=4.6 Hz), 117.92 (d, $J_{CF}$=13.1 Hz), 111.72, 102.50 (d, $J_{CF}$=27.7 Hz), 80.03, 42.82, 42.75, 33.04, 31.86, 31.73, 29.44, 29.35, 29.21, 29.13, 25.65, 24.26, 22.56, 22.52, 13.29 & 13.27; ¹⁹F NMR (377 MHz, CD₃OD): δ −108.77 (dd, $J_{HF}$=13.3 Hz, 9.3 Hz, 1F); LRMS (ESI): m/z 409.6 (100%, M-Na⁺+2H⁺); HPLC: 3.7 min.

Compound III: Sodium (RS)-4-Octanoylindane-2-carboxylate

Methyl (RS)-4-octanoyl-2-carboxylate (71 mg, 4%) was isolated as a side product in the preparation of its isomer, methyl (RS)-5-octanoyl-2-carboxylate. ¹H NMR (400 MHz, CDCl₃): δ 7.66 (d, J=7.6 Hz, 1H), 7.35 (d, J=7.4 Hz, 1H), 7.24 (dd, J=7.6, 7.6 Hz, 1H), 3.69 (s, 3H), 3.64 (A of ABX, J=18.0, 9.4 Hz, 1H), 3.48 (B of ABX, J=18.1, 7.3 Hz, 1H), 3.13-3.34 (m, 3H), 2.90 (t, J=7.5 Hz, 2H), 1.68 (tt, J=7.2, 7.2 Hz, 2H), 1.24-1.38 (m, 8H), 0.86 (t, J=6.9 Hz, 3H); ¹³C NMR (101 MHz, CDCl₃): δ 203.01, 176.79, 144.82, 143.67, 134.73, 129.30, 128.35, 127.83, 52.91, 44.06, 40.82, 38.71, 36.44, 32.73, 30.34, 30.19, 25.36, 23.64, 15.10. Methyl (RS)-4-octanoyl-2-carboxylate (71 mg, 0.24 mmol) was saponified according to the standard protocol to give (RS)-4-octanoyl-2-carboxylic acid (66 mg, 96%) as an off-white solid. ¹H NMR (400 MHz, CDCl₃): δ 7.69 (d, J=7.6 Hz, 1H), 7.39 (d, J=7.4 Hz, 1H), 7.26 (dd, J=7.6, 7.6 Hz, 1H), 3.67 (A of ABX, J=18.0, 9.0 Hz, 1H), 3.56 (B of ABX, J=18.0, 6.9 Hz, 1H), 3.19-3.39 (m, 3H), 2.93 (t, J=7.4 Hz, 2H), 1.70 (tt, J=7.3, 7.3 Hz, 2H), 1.24-1.38 (m, 8H), 0.88 (t, J=6.9 Hz, 3H). (RS)-4-Octanoyl-2-carboxylic acid (66 mg, 0.23 mmol) was converted to the sodium salt according to the standard protocol to give sodium (RS)-4-octanoyl-2-carboxylate (70 mg, 99%) as an off-white solid. mp 106-110° C., ¹H NMR (400 MHz, CD₃OD): δ 7.69 (d, J=7.8 Hz, 1H), 7.38 (d, J=7.4 Hz, 1H), 7.24 (dd, J=7.6, 7.6 Hz, 1H), 3.37-3.56 (m, 2H), 3.10-3.21 (m, 3H), 2.95 (t, J=7.3 Hz, 2H), 1.66 (tt, J=7.3, 7.3 Hz, 2H), 1.26-1.39 (m, 8H), 0.89 (t, J=6.8 Hz, 3H); ¹³C NMR (101 MHz, CD₃OD): δ 203.56, 182.93, 145.34, 143.96, 133.93, 128.26, 126.97, 126.42, 47.62, 39.89, 38.69, 36.70, 31.76, 29.21, 29.17, 24.55, 22.52, 13.28; LRMS (ESI): m/z 577.6 (strong, 2M-2Na⁺+3H⁺), 289.2 (100%, M-Na⁺+2H⁺); HPLC: 3.43 min.

Compound IV: Sodium (RS)-2-[4-Octanoylphenoxy]octanoate

1-[4-Hydroxyphenyl]-1-octanone (440 mg, 2.0 mmol) and ethyl (RS)-2-bromooctanoate (552 mg, 2.2 mmol) were reacted according to the procedure used for the preparation of Compound I to give Ethyl (RS)-2-[4-Octanoylphenoxy]octanoate (605 mg, 78%). ¹H NMR (400 MHz, CDCl₃): δ 7.91 (d, J=9.0 Hz, 2H), 6.88 (d, J=9.0 Hz, 2H), 4.66 (dd, J=5.1, 7.4 Hz, 1H), 4.20 (q, J=7.0 Hz, 2H), 2.88 (t, J=7.5 Hz, 2H), 1.88-2.02 (m, 2H), 1.70 (tt, J=7.2, 7.2 Hz, 2H), 1.41-1.56 (m, 2H), 1.25-1.37 (m, 14H), 1.23 (t, J=7.1 Hz, 3H), 0.87 (t, J=7.2 Hz, 3H), 0.86 (t, J=7.2 Hz, 3H); ¹³C NMR (101 MHz, CDCl₃): δ 199.41, 171.48, 161.81, 131.01, 130.54 (2C), 114.77 (2C), 76.75, 61.62, 38.56, 32.90, 31.94, 31.78, 29.60, 29.38, 29.07, 25.33, 24.80, 22.85, 22.75, 14.39, 14.31, 14.26. The resulting ester (605 mg, 1.6 mmol) was saponified with lithium hydroxide (186 mg, 7.8 mmol) according to the procedure used for the preparation of Compound I to give (RS)-2-[4-Octanoylphenoxy]octanoic Acid (487 mg, 87%). ¹H NMR (400 MHz, CDCl₃): δ 9.70 (br s, 1H), 7.89 (d, J=9.0 Hz, 2H), 6.89 (d, J=9.0 Hz, 2H), 4.69 (dd, J=5.9, 6.6 Hz, 1H), 2.87 (t, J=7.5 Hz, 2H), 1.95-2.01 (m, 2H), 1.67 (tt, J=7.2, 7.2 Hz, 2H), 1.43-1.58 (m, 2H), 1.24-1.37 (m, 14H), 0.851 (t, J=6.8 Hz, 3H), 0.849 (t, J=7.4 Hz, 3H); ¹³C NMR (101 MHz, CDCl₃): δ 200.38, 176.08, 161.84, 130.85, 130.78 (2C), 114.83 (2C), 76.20, 38.56, 32.79, 31.93, 31.76, 29.57, 29.35, 29.05, 25.34, 24.92, 22.84, 22.74, 14.29, 14.23. The acid (500 mg, 1.4 mmol) was then converted to the sodium salt according to the procedure used for the preparation of Compound I to give Sodium (RS)-2-[4-Octanoylphenoxy]octanoate (404 mg, 76%) as a white solid. mp 165-170° C.; ¹H NMR (400 MHz, CD₃OD): δ 7.91 (d, J=8.8 Hz, 2H), 6.95 (d, J=8.8 Hz, 2H), 4.58 (dd, J=6.1, 6.3 Hz, 1H), 2.91 (t, J=7.3 Hz, 2H), 1.91-1.96 (m, 2H), 1.62-1.69 (m, 2H), 1.44-1.58 (m, 2H), 1.25-1.39 (m, 14H), 0.87-0.90 (m, 6H); ¹³C NMR (101 MHz, CD₃OD): δ 200.50, 176.40, 162.96, 130.28 (2C), 129.94, 114.71 (2C), 78.38, 38.00, 32.98, 31.79, 31.74, 29.27, 29.20, 29.05, 25.50, 24.79, 22.56, 22.51, 13.36, 13.34; LRMS (ESI): m/z 769 (M₂H⁺), 748 (2M-Na⁺+2H⁺), 363 (M-Na⁺+2H⁺); HPLC: 3 min.

Compound V: Sodium (RS)-2-[4-Butyrylphenoxy]decanoate

1-[4-Hydroxyphenyl]-1-butanone (328 mg, 2.0 mmol) and ethyl (RS)-2-bromodecanoate (614 mg, 2.2 mmol) were reacted according to the procedure used for the preparation of Compound IV to give Ethyl (RS)-2-[4-Butyrylphenoxy]

decanoate (616 mg, 85%) as a clear, colourless oil. $^1$H NMR (400 MHz, CDCl$_3$): δ 7.88 (d, J=9.0 Hz, 2H), 6.86 (d, J=9.0 Hz, 2H), 4.64 (dd, J=5.7, 6.8 Hz, 1H), 4.17 (q, J=7.2 Hz, 2H), 2.83 (t, J=7.3 Hz, 2H), 1.85-1.99 (m, 2H), 1.65-1.75 (m, 2H), 1.39-1.44 (m, 2H), 1.22-1.34 (m, 10H), 1.20 (t, J=7.2 Hz, 3H), 0.94 (t, J=7.4 Hz, 3H), 0.83 (t, J=7.0 Hz, 3H); $^{13}$C NMR (101 MHz, CDCl$_3$): δ 199.04, 171.39, 161.80, 130.98, 130.48 (2C), 114.74 (2C), 76.68, 61.55, 40.37, 32.85, 32.01, 29.53, 29.37 (2C), 25.33, 22.84, 18.11, 14.34, 14.29, 14.10. The resulting ester (616 mg, 1.70 mmol) was saponified with lithium hydroxide (203 mg, 8.5 mmol) according to the procedure used for the preparation of Compound IV to give (RS)-2-[4-Butyrylphenoxy]decanoic Acid (166 mg, 29%). $^1$H NMR (400 MHz, CDCl$_3$): δ 10.06 (br s, 1H), 7.91 (d, J=9.0 Hz, 2H), 6.90 (d, J=9.0 Hz, 2H), 4.70 (dd, J=5.9, 6.4 Hz, 1H), 2.87 (t, J=7.3 Hz, 2H), 1.96-2.02 (m, 2H), 1.68-1.77 (m, 2H), 1.44-1.59 (m, 2H), 1.24-1.37 (m, 10H), 0.97 (t, J=7.4 Hz, 3H), 0.86 (t, J=7.0 Hz, 3H); $^{13}$C NMR (101 MHz, CDCl$_3$): δ 199.95, 176.56, 161.74, 131.03, 130.73 (2C), 114.82 (2C), 76.16, 40.47, 32.79, 32.03, 29.53, 29.39, 29.37, 25.38, 22.86, 18.26, 14.31, 14.12. The acid (166 mg, 0.5 mmol) was then converted to the sodium salt according to the procedure used for the preparation of Compound IV to give Sodium (RS)-2-[4-Butyrylphenoxy]decanoate (149 mg, 85%) as a white solid. mp 262-278° C.; $^1$H NMR (400 MHz, CD$_3$OD): δ 7.91 (d, J=9.0 Hz, 2H), 6.96 (d, J=9.0 Hz, 2H), 4.70 (dd, J=6.1, 6.5 Hz, 1H), 2.90 (t, J=7.3 Hz, 2H), 1.88-1.93 (m, 2H), 1.67 (tq, J=7.4, 7.4 Hz, 2H), 1.41-1.57 (m, 2H), 1.20-1.35 (m, 10H), 0.95 (t, J=7.4 Hz, 3H), 0.83 (t, J=6.9 Hz, 3H); $^{13}$C NMR (101 MHz, CD$_3$OD): δ 201.82, 178.07, 163.36, 130.53 (2C), 129.54, 114.83 (2C), 79.46, 39.99, 33.11, 31.80, 29.40, 29.27, 29.15, 25.72, 22.54, 18.30, 14.46, 14.15; LRMS (ESI): m/z 713 (M$_2$H$^+$), 669 (2M-2Na$^+$+3H$^+$), 335 (M-Na$^+$2H$^+$); HPLC: 3 min.

Compound VI: Sodium
(RS)-2-[4-Hexanoylphenoxy]decanoate

1-[4-Hydroxyphenyl]-1-hexanone (384 mg, 2.0 mmol) and ethyl (RS)-2-bromodecanoate (614 mg, 2.2 mmol) were reacted according to the procedure used for the preparation of Compound IV to give Ethyl (RS)-2-[4-Hexanoylphenoxy]decanoate (628 mg, 80%). $^1$H NMR (400 MHz, CDCl$_3$): δ 7.86 (d, J=9.0 Hz, 2H), 6.84 (d, J=9.0 Hz, 2H), 4.60-4.65 (m, 1H), 4.15 (q, J=7.0 Hz, 2H), 2.83 (t, J=7.3 Hz, 2H), 1.86-1.97 (m, 2H), 1.61-1.70 (m, 2H), 1.38-1.52 (m, 2H), 1.20-1.34 (m, 14H), 1.18 (t, J=7.2 Hz, 3H), 0.78-0.87 (m, 6H); $^{13}$C NMR (101 MHz, CDCl$_3$): δ 199.17, 171.36, 161.78, 130.95, 130.46 (2C), 114.72 (2C), 76.66, 61.51, 38.41, 32.84, 32.00, 31.76, 29.52, 29.35 (2C), 25.31, 24.41, 22.83, 22.74, 14.33, 14.26, 14.14. The resulting ester (628 mg, 1.6 mmol) was saponified with lithium hydroxide (193 mg, 8.0 mmol) according to the procedure used for the preparation of Compound IV to give (RS)-2-[4-Hexanoylphenoxy]decanoic Acid (468 mg, 80%). $^1$H NMR (400 MHz, CDCl$_3$): δ 7.93 (d, J=9.0 Hz, 2H), 6.91 (d, J=9.0 Hz, 2H), 5.77 (br s, 1H), 4.70 (dd, J=5.8, 6.6 Hz, 1H), 2.89 (t, J=7.4 Hz, 2H), 1.97-2.03 (m, 2H), 1.67-1.74 (m, 2H), 1.44-1.60 (m, 2H), 1.23-1.37 (m, 14H), 0.90 (t, J=6.8 Hz, 3H), 0.87 (t, J=7.0 Hz, 3H); $^{13}$C NMR (101 MHz, CDCl$_3$): δ 199.76, 176.29, 161.56, 131.20, 130.70 (2C), 114.81 (2C), 76.12, 38.56, 32.78, 32.03, 31.80, 29.53, 29.40, 29.36, 25.36, 24.51, 22.87, 22.76, 14.33, 14.20. The acid (468 mg, 1.3 mmol) was then converted to the sodium salt according to the procedure used for the preparation of Compound IV to give Sodium (RS)-2-[4-Hexanoylphenoxy]decanoate (459 mg, 93%) as a white solid. mp 275-280° C.; $^1$H NMR (400 MHz, CD$_3$OD): δ 7.91 (d, J=8.8 Hz, 2H), 6.96 (d, J=8.8 Hz, 2H), 4.44-4.48 (m, 1H), 2.89-2.96 (m, 2H), 1.88-1.96 (m, 2H), 1.63-1.71 (m, 2H), 1.44-1.61 (m, 2H), 1.24-1.38 (m, 14H), 0.84-0.93 (m, 6H); $^{13}$C NMR (101 MHz, CD$_3$OD): δ 200.89, 177.86, 163.36, 130.27 (2C), 129.60, 114.75 (2C), 79.54, 37.94, 33.18, 31.86, 31.49, 29.44, 29.38, 29.21, 25.73, 24.55, 22.58, 22.45, 13.36, 13.23; LRMS (ESI): m/z 769.8 (M$_2$H$^+$), 747.8 (2M-Na$^+$+2H$^+$), 363.2 (M-Na$^+$+2H$^+$); HPLC: 3.min.

Compound VII: Sodium
(RS)-2-[4-Octanoylbenzyl]decanoate

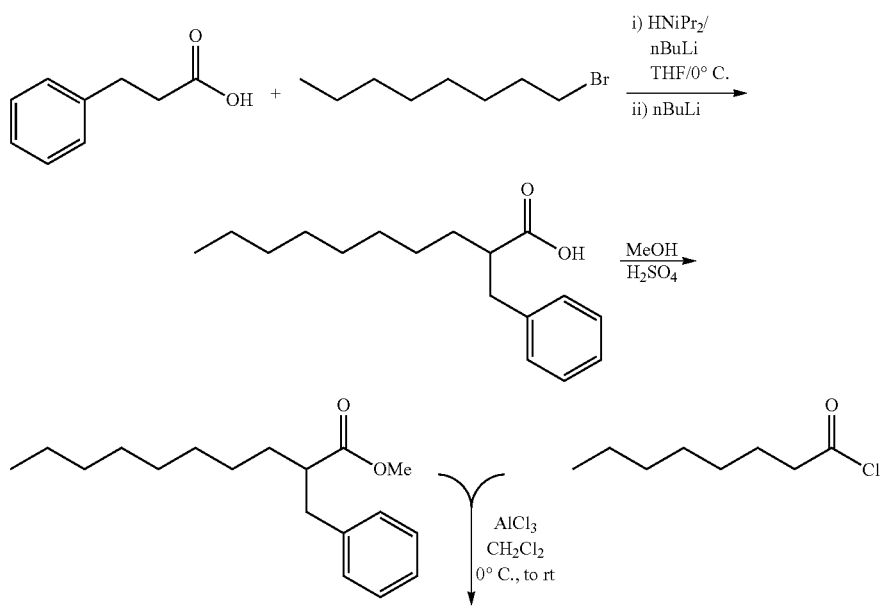

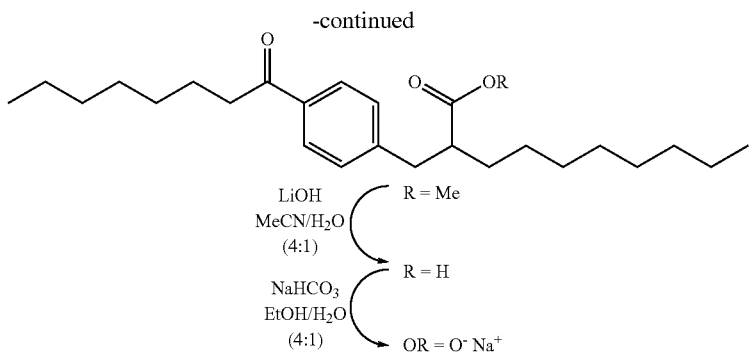

Step 1

A solution of diisopropylamine (1.5 mL, 10.5 mmol) in anhydrous tetrahydrofuran (20 ml) was cooled to 0° C. under nitrogen, and was treated with a solution of n-butyllithium in hexanes (2.3M; 4.4 mL, 10.0 mmol). After 5 min a solution of 3-phenylpropanoic acid (1.5 g, 10.0 mmol) in anhydrous tetrahydrofuran (10 mL) was added, to give a white suspension. After 20 min at 0° C., the reaction was cooled to −10° C. and a second portion of n-butyllithium in hexanes (2.3M; 4.80 mL, 11.0 mmol) was added. Stirring at −10° C. for 10 min, then at room temperature for 40 min gave a clear, pale brown solution. The solution was cooled to 0° C. and was treated with 1-bromooctane (1.8 mL, 10.5 mmol). The reaction was stirred at 00° C. for 20 min and then at room temperature for 3 h. A solution of saturated aqueous ammonium chloride (100 mL) was added; the pH was adjusted to 1 with aqueous hydrochloric acid (6M); and the mixture was extracted with ethyl acetate (100 mL). The organic extract was washed with water (100 mL) and with saturated aqueous sodium chloride (75 mL); then dried over sodium sulfate; filtered and evaporated in vacuo to give the crude product. Purification on a Biotage™ 40 L cartridge (silica), eluting with 0-20% ethyl acetate in hexanes gave (RS)-2-benzyldecanoic acid as a straw-coloured oil (1.9 g, 73%). $^1$H NMR (400 MHz, CDCl$_3$): δ 11.51 (br s, 1H), 7.14-7.35 (m, 5H), 3.00 (dd, J=13.7, 7.9 Hz, 1H), 2.77 (dd, J=13.7, 6.8 Hz, 1H), 2.65-2.72 (m, 1H), 1.62-1.71 (m, 1H), 1.49-1.57 (m, 1H), 1.20-1.42 (m, 12H), 0.90 (t, J=6.8 Hz, 3H).

Step 2

A solution of the carboxylic acid compound (1.9 g, 7.3 mmol) in methanol (13 mL) was treated with sulfuric acid (0.35 mL, 6.6 mmol), and the reaction was stirred at room temperature overnight. The reaction was then diluted with ethyl acetate (175 mL), and the solution was washed with aqueous sodium (0.5M) hydroxide solution (175 mL), with water (175 mL), and with saturated sodium chloride solution (135 mL); then dried over sodium sulfate; filtered and evaporated in vacuo to give methyl (RS)-2-benzyldecanoate as a golden yellow oil (2.0 g, 99%). $^1$H NMR (400 MHz, CDCl$_3$): δ 7.14-7.29 (m, 5H), 3.60 (s, 3H), 2.93 (dd, J=13.4, 8.4 Hz, 1H), 2.74 (dd, J=13.6, 6.5 Hz, 1H), 2.62-2.69 (m, 1H), 1.60-1.67 (m, 1H), 1.45-1.55 (m, 1H), 1.22-1.37 (m, 12H), 0.88 (t, J=6.8 Hz, 3H).

Step 3

A solution of the methyl ester compound (1.5 g, 5.5 mmol) and octanoyl chloride (1.4 mL, 8.3 mmol) in anhydrous dichloromethane (25 mL) was cooled to 00° C. under nitrogen, and was treated with aluminum chloride granules (2.2 g, 16.6 mmol) in small portions over 160 min. The reaction was stirred at 0° C. for 150 min and was then quenched by pouring into a mixture of ice (150 mL) and water (150 mL). The mixture was stirred for 10 min and was then extracted with ethyl acetate (150 mL). The organic extract was washed with aqueous sodium hydroxide solution (0.5M, 200 mL) and with saturated sodium chloride solution (100 mL); and was then dried over sodium sulfate; filtered and evaporated in vacuo to give the crude compound. Purification on a Biotage™ 40 L cartridge (silica), eluting with 0-3% ethyl acetate in hexanes gave methyl (RS)-2-[4-octanoylbenzyl]decanoate as a yellow oil (157 mg, 7%). $^1$H NMR (400 MHz, CDCl$_3$): δ 7.83 (d, J=8.2 Hz, 2H), 7.19 (d, J=8.2 Hz, 2H), 3.54 (s, 3H), 2.93 (dd, J=13.6, 8.8 Hz, 1H), 2.88 (t, J=7.4 Hz, 2H), 2.75 (dd, J=13.6, 6.2 Hz, 1H), 2.60-2.68 (m, 1H), 1.58-1.71 (m, 3H), 1.42-1.50 (m, 1H), 1.18-1.35 (m, 20H), 0.84 (t, J=6.8 Hz, 3H), 0.83 (t, J=6.8 Hz, 3H); $^{13}$C NMR (101 MHz, CDCl$_3$): δ 200.21, 175.88, 145.12, 135.58, 129.19, 128.43, 51.57, 47.51, 38.69, 38.59, 32.47, 32.02, 31.92, 29.63, 29.57, 29.55, 29.40, 29.37, 27.46, 24.58, 22.84, 22.83, 14.28 & 14.26.

Step 4

A solution of the methyl ester compound (156 mg, 0.3 mmol) in acetonitrile (4 mL) was treated with a solution of lithium hydroxide (46 mg, 1.9 mmol) in water (1 mL) and the reaction was stirred at room temperature for 3 days, at 60° C. for 20 h, and then at room temperature for a further 4 days. The reaction mixture was partitioned between ethyl acetate (20 mL) and aqueous hydrochloric acid (1M, 20 mL). The organic phase was washed with water (20 mL) and with saturated aqueous sodium chloride solution (20 mL); then dried over sodium sulfate; filtered and evaporated in vacuo to give a partially hydrolysed mixture of methyl ester and carboxylic acid. Purification on a Biotage™ 12M cartridge (silica), eluting with 0-30% ethyl acetate in hexanes gave (RS)-2-[4-octanoylbenzyl]decanoic acid as a colourless oil (46 mg, 31%). $^1$H NMR (400 MHz, CDCl$_3$): δ 7.88 (d, J=8.2 Hz, 2H), 7.26 (d, J=8.2 Hz, 2H), 3.01 (dd, J=13.8, 8.1 Hz, 1H), 2.93 (t, J=7.4 Hz, 2H), 2.81 (dd, J=13.8, 6.5 Hz, 1H), 2.65-2.72 (m, 1H), 1.61-1.75 (m, 3H), 1.46-1.55 (m, 1H), 1.23-1.40 (m, 20H), 0.88 (t, J=6.9 Hz, 3H), 0.87 (t, J=6.7 Hz, 3H).

Step 5

A solution of sodium bicarbonate (10 mg, 0.12 mmol) in water (0.25 mL) was treated with a solution of the carboxylic acid (46 mg, 0.12 mmol) in ethanol (1.0 mL), and the reaction was stirred at room temperature overnight. Solvents were evaporated in vacuo, and the residue was dissolved in water (4 mL), filtered (0.2 micron, PES), and lyophilized to give a gum. Evaporation from acetone solution gave sodium (RS)-2-[4-octanoylbenzyl]decanoate as an off-white solid (45 mg, 93%). $^1$H NMR (400 MHz, CD$_3$OD): δ 7.86 (d, J=8.4 Hz, 2H), 7.35 (d, J=8.4 Hz, 2H), 2.94-3.00 (m, 3H), 2.69 (dd, J=13.3, 6.6 Hz, 1H), 2.46-2.53 (m, 1H), 1.54-1.70 (m, 3H), 1.23-1.40 (m, 21H), 0.89 (t, J=6.8 Hz, 3H), 0.87 (t, J=7.2 Hz, 3H); $^{13}$C NMR (101 MHz, CD$_3$OD): δ 201.60, 182.80, 147.71, 134.81, 129.26, 128.04, 51.14, 39.54, 38.24, 33.04, 31.92, 31.77, 29.76, 29.52, 29.27, 29.23, 29.18, 27.78, 24.62, 22.57, 22.54, 13.33 & 13.31; LRMS (ESI): m/z 389.7 (100%, [M-Na$^+$+2H$^+$]); HPLC: 3.2 min.

Example 2: Effect of Compounds on LPS-Stimulated RAW264.7 Cells; an Osteoclast Progenitor LPS, a bacteria-derived cell wall product, has long been recognized as a key factor in the development of bone loss. LPS plays an important role in bone resorption, which involves recruitment of inflammatory cells, synthesis of cytokines (such as interleukin-6 (IL-6), IL-12 and tumor necrosis factor-a (TNF-a)), and activation of osteoclast formation and differentiation.

RAW264 cells are precursors of osteoclasts and can be differentiated by several factors including Receptor activator of NF-κB ligand (RANKL) or Lipopolysaccharide (LPS). Osteoclasts are characterized by high expression or tartrate resistant acid phosphatase (TRACP) and Matrix Metalloproteinase-9 (MMP-9) which can be used as markers for osteoclasts. It has been shown that RAW264.7 cells incubated in presence of capric acid resulted in an increase in IL-12 production and in a reduction of phosphatase (TRAP)-positive cells (TRAP expression, an osteoclast differentiation marker) (Wang et al., J. Biol. Chem. (2006), Vol. 281, No. 45, pp. 34457-64). Furthermore, LPS strongly upregulated inducible nitric oxide synthase (iNOS) mRNA levels and nitric oxide (NO) production, whereas capric acid inhibited them. Additionally, capric acid also inhibited monocyte chemoattractant protein-1 (MCP-1) mRNA expression.

The effect of compounds of Formula I on TRAP (osteoclast marker) and IL-12 can be undertaken in RAW264.7 cells, a murine osteoclast precursor cell line. RAW264.7 cells are differentiated by the incubation with LPS (1 ug/ml) in presence or not of capric acid (positive control) or the compound(s) to be tested. Osteoclast formation is evaluated on days 3-5, using tartrate-resistant acid phosphatase (TRAP) staining.

The osteoclastogenesis effect of LPS in RAW264.7 cells is demonstrated by the high expression of TRAP (dark staining). If no or less TRAP cells are observable when contacted with the tested compound(s), this indicates that the cells are not differentiated in osteoclasts, suggesting that the tested compound(s) inhibit osteoclastogenesis.

It is has also been reported that capric acid increases the production of IL-12 in LPS-stimulated RAW264.7 (Wang et al., J. Biol. Chem. (2006), Vol. 281, No. 45, pp. 34457-64). Since capric acid is also a known osteoclastogenesis inhibitor, experiments may be undertaken to determine if compounds of Formula I are capable of promoting an increase in IL-12 production. Accordingly, RAW264.7 cells are cultured with 100 ng/mL of LPS in presence or absence of the compound(s) for 21 h in a humidified atmosphere of 95% air-5% carbon dioxide at 37° C. IL-12 concentration in the culture medium is measured using the IL-12 ELISA according to the manufacturer (BD Biosciences) recommendations. A strong induction of IL-12 production in LPS-stimulated RAW264.7 cells in presence of various concentrations of the tested compounds would confirm that the compounds are capable of promoting an increase in IL-12 production.

Example 3: Effect of Compounds of Formula I on IL-12 Production in LPS-Stimulate RAW264.7 Cells; an Osteoclast Progenitor IL-12 is also reported to inhibit osteoclast formation (Horwood and al., 2001, J. of Immunology, Volume 166, No. 8, pp. 4915-4921). As mentioned in Example 1, LPS-stimulated RAW264.7 incubated in presence of compounds of Formula I may increase IL-12 and reduce osteoclastogenesis (TRAP). Accordingly, an in vitro IL-12 production assay was used for screening potential inhibitors of osteoclastogenesis. Table 1 represents the effect of representative compounds of Formula I on IL-12 production. All tested compounds induced a significant increase in IL-12 production.

TABLE 1

Effect of representative compounds of Formula I on IL-12 production

| Compound | Structure | IL-12 pg/mL | Compound Concentration |
|---|---|---|---|
| I | (structure) | 112 | 0.0075 mM |
| II | (structure) | 20 | 0.008 mM |

TABLE 1-continued

Effect of representative compounds of Formula I on IL-12 production

| Compound | Structure | IL-12 pg/mL | Compound Concentration |
|---|---|---|---|
| III | 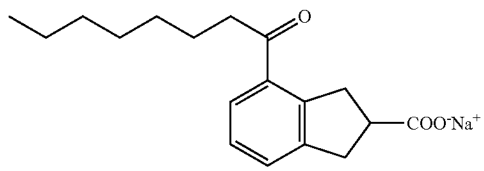 | 24.95 | 0.1 mM |
| IV | 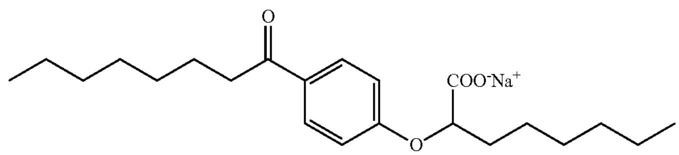 | 12.13 | 0.020 mM |
| V | 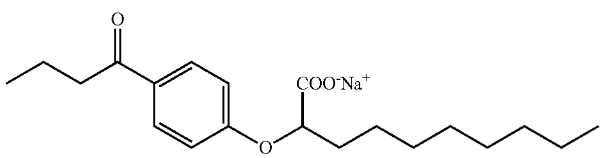 | 73.32 | 0.040 mM |
| VI | 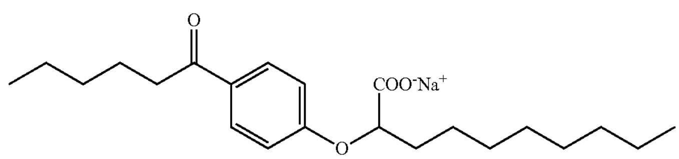 | 53.5 | 0.020 mM |
| VII | 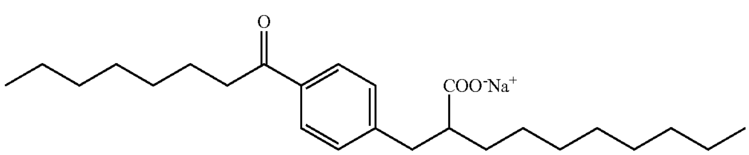 | 8 | 0.012 mM |

These results demonstrate that the tested compounds induce the production of IL-12, in the presence of LPS. The ability to simulate the production of IL-12 means that compounds of the present invention may be useful for preventing and/or treating osteoporosis as a result of the induction of IL-12. This is supported by the references mentioned above in example 2, which teach that IL-12 has a direct inhibitory effect on osteoclastogenesis.

Example 4: Effect of Compound I on the Reduction of Osteoporosis in an Ovariectomized-Rat Model Although in comparison to humans, the skeletal mass of rats remains stable for a protracted period during their lifespan, rats can be ovariectomized to make them sex-hormone deficient, and to stimulate the accelerated loss of bone that occurs in women following menopause. Ovariectomy induced bone loss in the rat and postmenopausal bone loss share many similar characteristics. These include: increased rate of bone turnover with resorption exceeding formation; an initial rapid phase of bone loss followed by a much slower phase; greater loss of cancellous than cortical bone; decreased intestinal absorption of calcium; some protection against bone loss by obesity; and similar skeletal response to therapy with estrogen, tamoxifen, bisphosphonates, parathyroid hormone, calcitonin and exercise. These wide-ranging similarities are strong evidence that the ovariectomized rat bone loss model is suitable for studying problems that are relevant to postmenopausal bone loss.

Sprague Dawley rats (250 g) were ovariectomized (OVX) at day 0. Rats were treated by oral gavage with Compound I (10 mg/kg) from day 14 to day 68. Evaluation of different parameters (body weight, calcium loss, osteoclast markers (RANKL and TRAP mRNA expression), collagen content and histology was performed at day 68.

FIG. 1 illustrates the increase in body weight increase in the ovariectomized rats (similar to the "postmenopausal obesity"). Compound I reduced ovariectomized-induced obesity.

Figure 2:
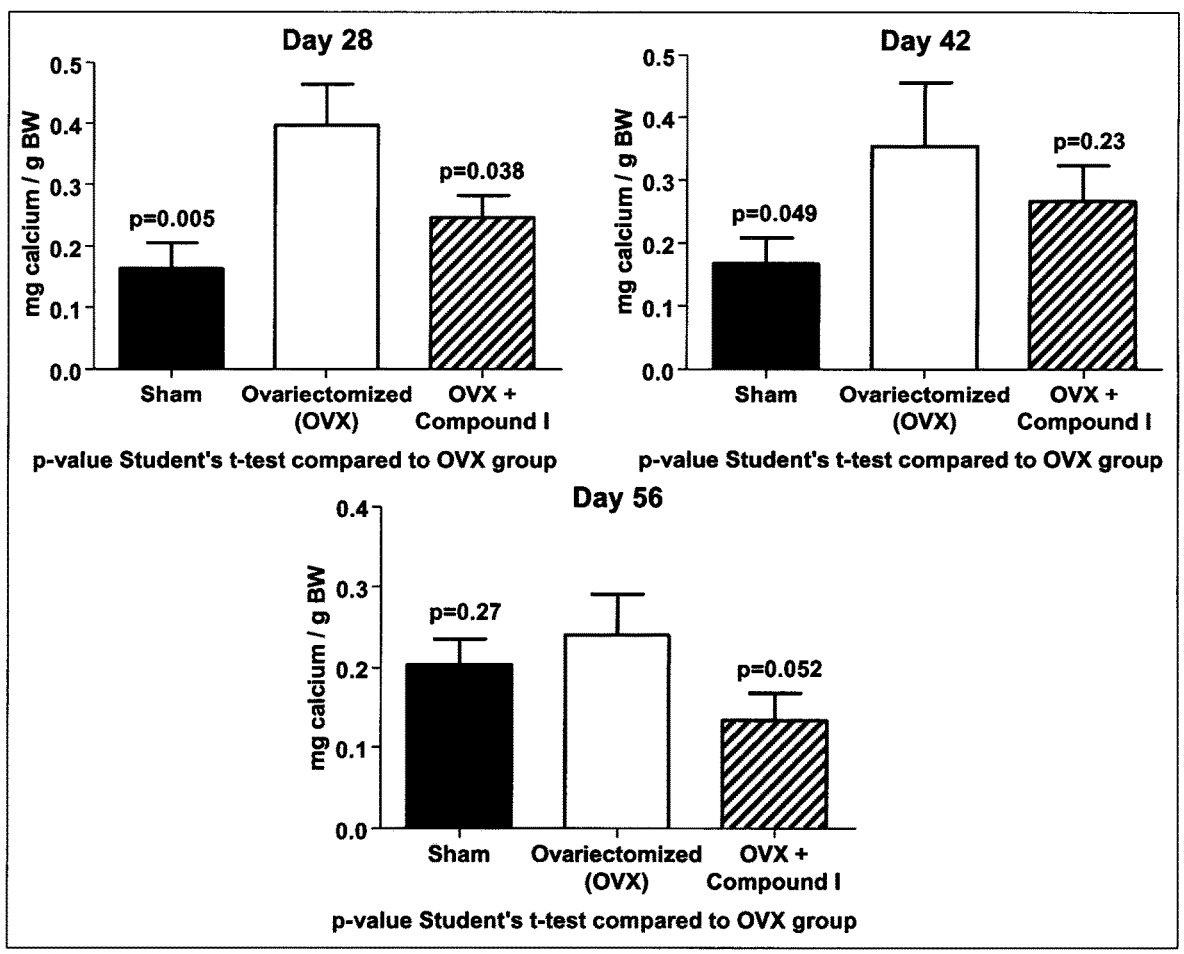
FIG. 2 is a panel with bar graphs demonstrating the effect of Compound I on calcium in urine of ovariectomized (OVX) rats, according to Example 4.

FIG. 2 represents the effect of Compound I on calcium loss in ovariectomized rats. Calcium loss is detected in urine from ovariectomized rats from day 28 to day 56. Compound I reduced significantly the calcium loss in ovariectomized rats.

Figure 3:
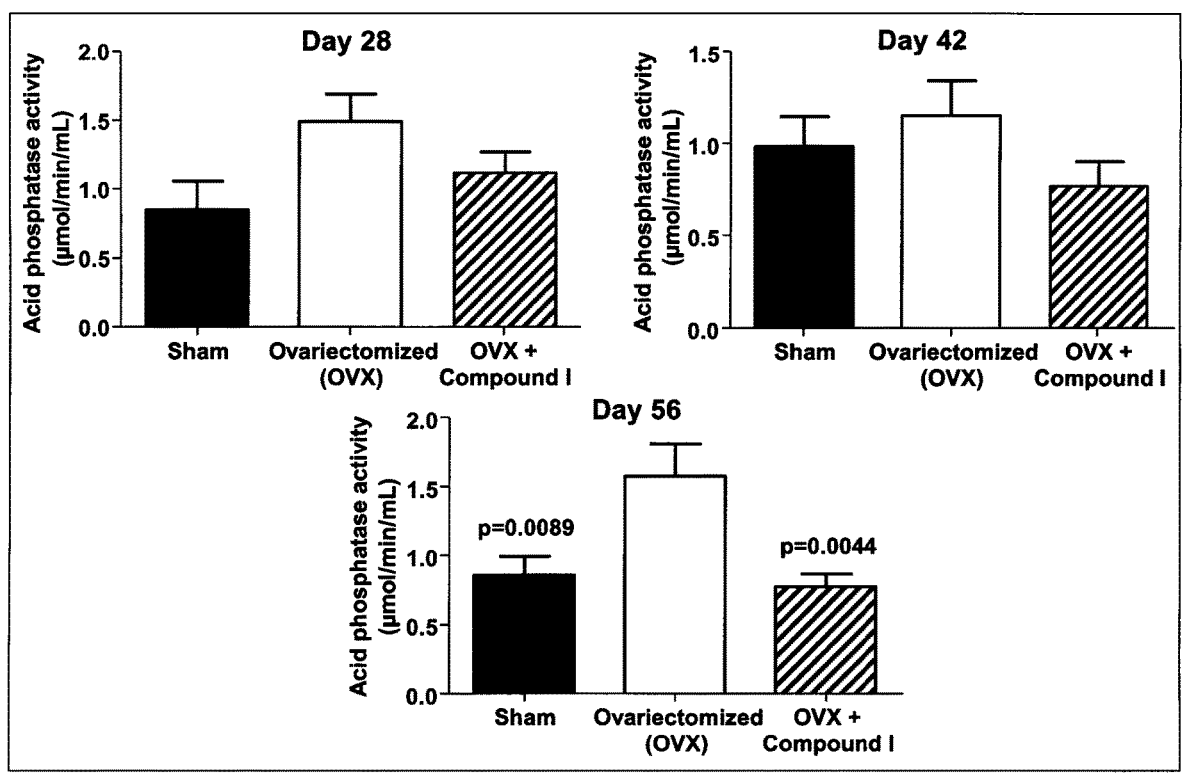
FIG. 3 a panel with bar graphs demonstrating the effect of Compound I on acid phosphatase activity in serum of ovariectomized (OVX) rats, according to Example 4.

Furthermore, it is known that acid phosphatase activity in serum is an indication of osteoclastogenesis (Park et al. (2011) PLOS One Volume 6, Issue 11, pp. 1-8). Serum acid phosphatase activity was measured and this activity increased significantly in ovariectomized rats from day 28 to day 56 (FIG. 3). However, Compound I reduced the acid phosphatase activity in the serum of ovariectomized rats (FIG. 3); a decrease is indicative of a successful reduction in osteoclastogenesis.

Figure 4:
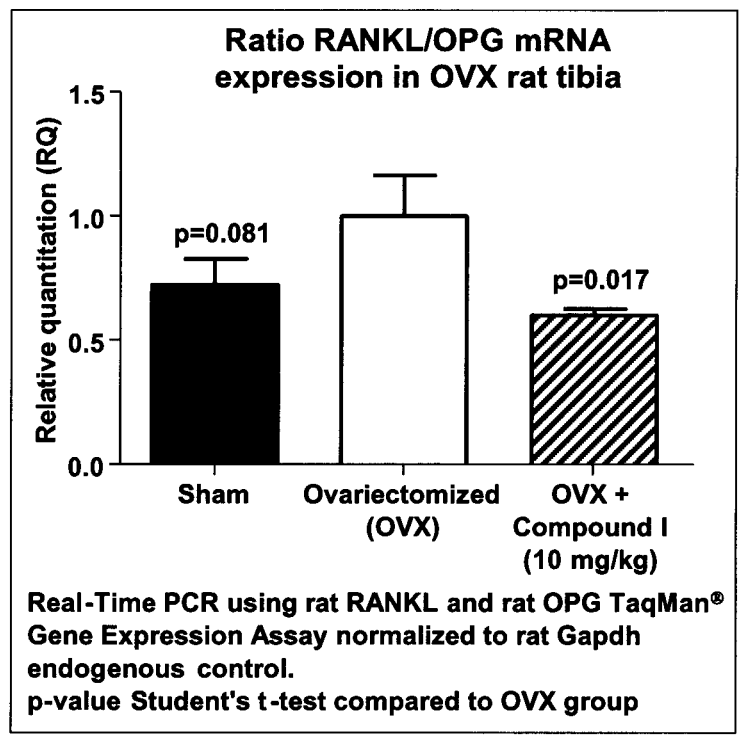
FIG. 4 is a bar graph demonstrating the effect of Compound I on RANKL/OPG mRNA expression of osteoclast marker in ovariectomized (OVX) rat tibia, according to Example 4.

FIG. 4 represents the effect of Compound I on the ratio of mRNA expression of RANKL/OPG at day 68 in rat tibia. As shown, RANKL/OPG mRNA expression increased in rats developing osteoporosis while it decreased with the treatment with Compound I; a decrease is indicative of a successful reduction of osteoclastogenesis.

Figure 5:
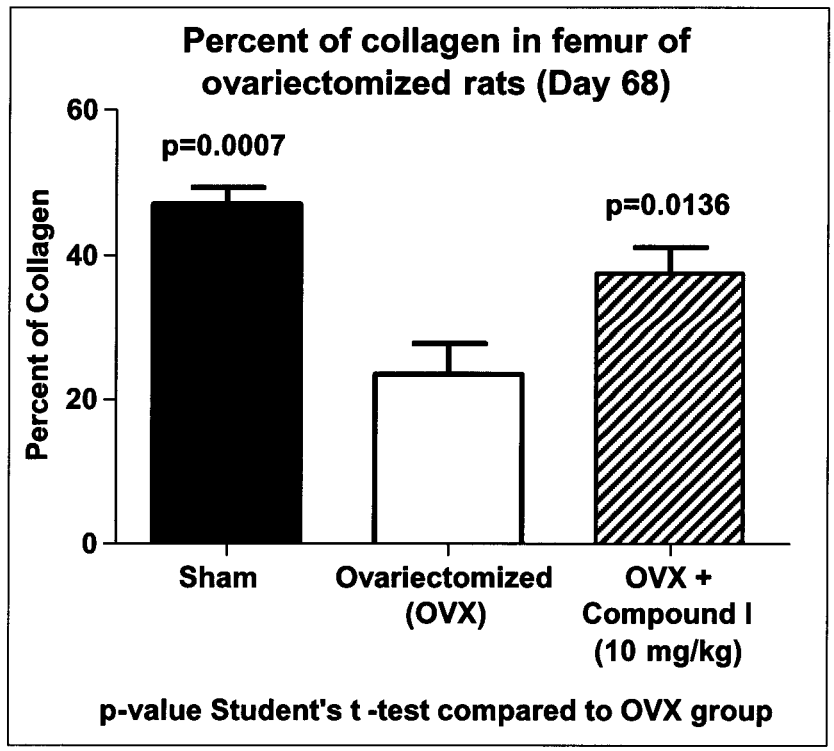
FIG. 5 is a bar graph demonstrating the effect of Compound I on collagen content in metaphyse of rat's femur, according to Example 4.

As a result of bone loss, collagen content is decreased. This was observed in ovariectomized rats. Compound I increased the collagen content in the metaphyse of the femur of ovariectomized rats, suggesting a reduction of bone loss (FIG. 5).

Figure 6:
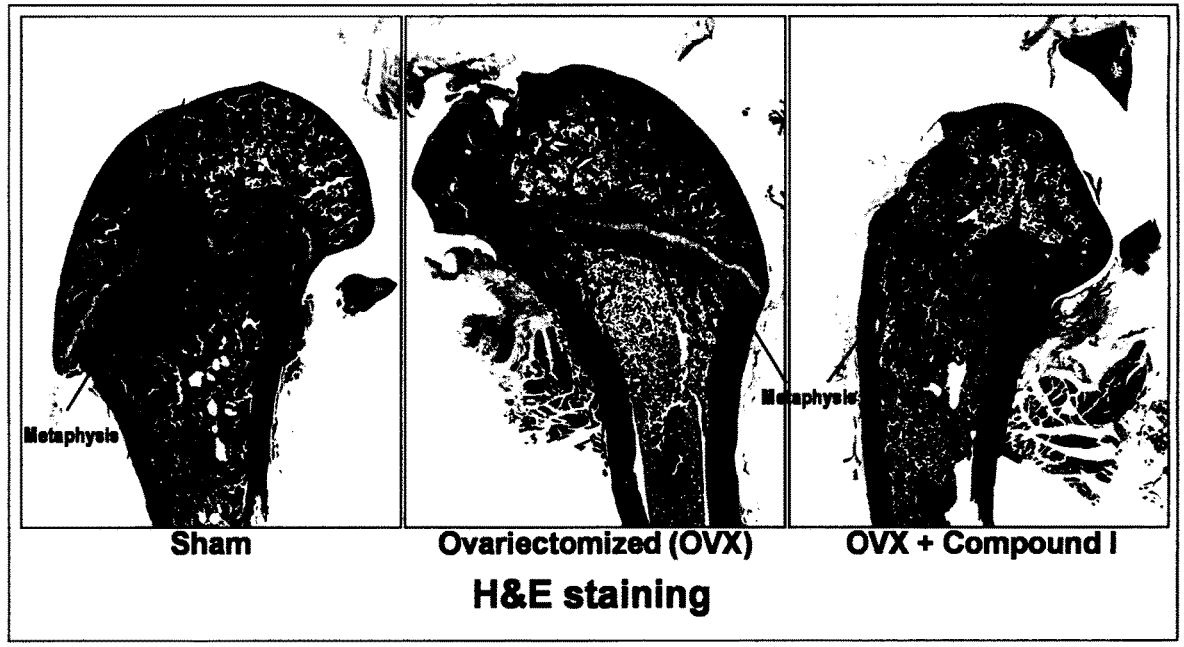
FIG. 6 is a panel with pictures illustrating the effect of Compound I on collagen content in metaphyse of rat's femur, according to Example 4.
Figure 7:
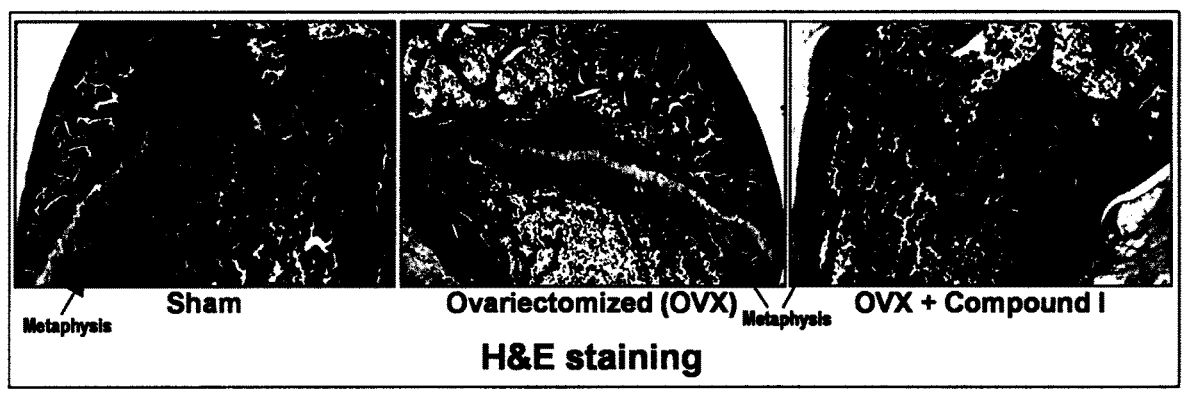
FIG. 7 is a panel with enlarged pictures corresponding to the pictures of FIG. 6.

FIGS. 6 and 7 show representative pictures of histological bone section of the metaphysis of the femur. Compound I reduced bone loss in the metaphysis portion of the femur.

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method for the treatment of primary type 1 osteoporosis, primary type 2 osteoporosis, or secondary osteoporosis, comprising the step of administering to a subject in need thereof a compound represented by Formula I or a pharmaceutical acceptable salt thereof:

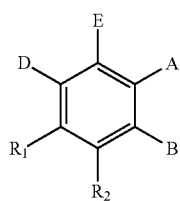

Formula I wherein:
$R_1$ and $R_2$ are independently H, F or OH;
A is H, $(CH_2)_m COOH$, $W(CH_2)_m COOH$ or

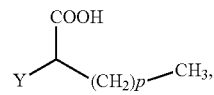

and B is H, $(CH_2)_m COOH$, $W(CH_2)_m COOH$ or

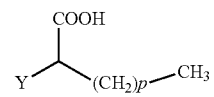

with the proviso that A is $(CH_2)_m COOH$, $W(CH_2)_m COOH$ or

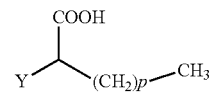

when B is H; and B is $(CH_2)_m COOH$, $W(CH_2)_m COOH$ or

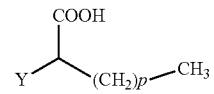

when A is H; or A and B are covalently bonded to form a five (5), six (6) or seven (7)-membered cycloalkyl substituted with COOH;
wherein:
Y is O, S, NH, or $CH_2$;
W is O, S, or NH;
m is 0-2; and
p is 3-7;
D is $C(O)-(CH_2)_n-CH_3$ or $CH(OH)-(CH_2)_n-CH_3$ or $O-(CH_2)_n-CH_3$ wherein n is 2-6; and
E is H or F.

2. The method of claim 1, wherein $R_1$ is H and $R_2$ is H.
3. The method of claim 1, wherein E is H.
4. The method of claim 1, wherein m is 1 or 2.
5. The method of claim 1, wherein A is H and B is

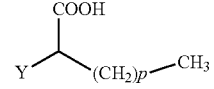

wherein Y is O, and p is 5-7.

6. The method of claim 1, wherein $R_1$ and $R_2$ are H; B is H; A is

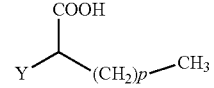

wherein p is 5-7, Y is O, and E is H.

7. The method of claim 1, wherein $R_1$ and $R_2$ are H; A is H; B is

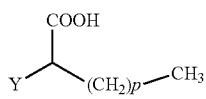

wherein p is 5-7, Y is O, and E is H.

8. The method of claim 1, wherein D is C(O)—(CH$_2$)$_n$—CH$_3$.

9. The method of claim 1, wherein n is 4-6.

10. The method of claim 1, wherein said compound is selected from the group consisting of the compounds represented by the following structures:

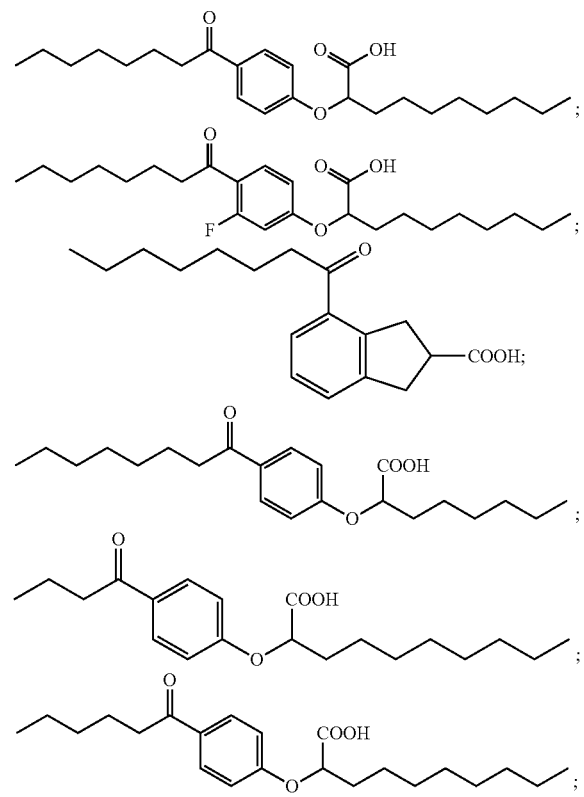

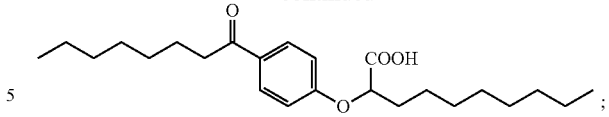

and pharmaceutically acceptable salts thereof.

11. The method of claim 10, wherein said compound is represented by the following structure:

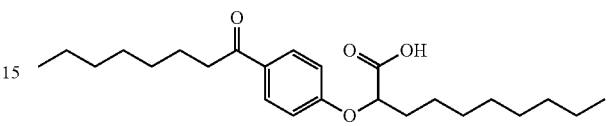

or pharmaceutically acceptable salt thereof.

12. The method of claim 1, wherein the pharmaceutically acceptable salt is a base addition salt comprising a metal counterion selected from the group consisting of sodium, potassium, calcium, magnesium lithium, ammonium, manganese, zinc, iron, or copper.

13. The method of claim 12, wherein the pharmaceutically acceptable salt is sodium.

14. The method of claim 1, wherein the osteoporosis is primary type 2 osteoporosis.

15. The method of claim 1, wherein the osteoporosis is post-menopausal osteoporosis (primary type 1).

16. The method of claim 1, wherein administration of said compound results in one or more of the following biological activities in the subject:
   inhibition of osteoclastogenesis;
   stimulation interleukin-12 (IL-12) production in bone;
   reduction of acid phosphatase activity in bone;
   reduction of Receptor activator of NF-κB ligand/Osteoprotegerin ratio (RANKL/OPG ratio) in bone;
   increase of collagen content in bone.

17. The method of claim 1, further comprising the step of administering concomitantly a drug selected from the group consisting of:
   bisphosphonates, Odanacatib, Alendronate, Risedronate, Etidronate, Zoledronate, Pamidronate, Teriparatide, Tamoxifen, Raloxifene, and Denosumab.

* * * * *

UNITED STATES PATENT AND TRADEMARK OFFICE
CERTIFICATE OF CORRECTION

Page 1 of 1

PATENT NO. : 10,925,846 B2
APPLICATION NO. : 15/516635
DATED : February 23, 2021
INVENTOR(S) : Gagnon et al.

It is certified that error appears in the above-identified patent and that said Letters Patent is hereby corrected as shown below:

In the Claims

In Claim 10, Column 34, Lines 2-7, delete the following structure:

" 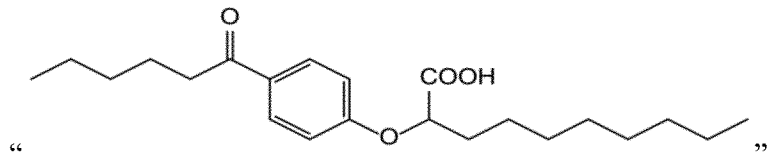 ”

And insert the following structure in its place:

-- 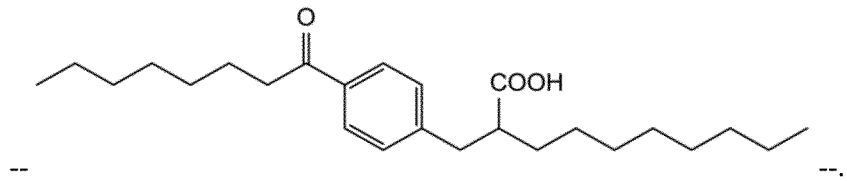 --.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*